United States Patent
Riber et al.

(10) Patent No.: US 10,457,714 B2
(45) Date of Patent: Oct. 29, 2019

(54) ACYLATED GLUCAGON ANALOGUES

(71) Applicant: Zealand Pharma A/S, Glostrup (DK)

(72) Inventors: Ditte Riber, Brønshøj (DK); Jakob Lind Tolborg, Herlev (DK); Dieter Wolfgang Hamprecht, Pozzolengo (IT); Wolfgang Rist, Ingelheim am Rhein (DE)

(73) Assignee: Zealand Pharma A/S, Søborg (DK)

( * ) Notice: Subject to any disclaimer, the term of this patent is extended or adjusted under 35 U.S.C. 154(b) by 0 days.

(21) Appl. No.: 15/852,458

(22) Filed: Dec. 22, 2017

(65) Prior Publication Data

US 2018/0141990 A1 May 24, 2018

Related U.S. Application Data

(63) Continuation of application No. 14/517,497, filed on Oct. 17, 2014, now Pat. No. 9,896,495.

(60) Provisional application No. 61/892,256, filed on Oct. 17, 2013.

(51) Int. Cl.
| | | |
|---|---|---|
| *A61K 38/00* | (2006.01) | |
| *C07K 14/605* | (2006.01) | |
| *A61K 38/26* | (2006.01) | |
| *A61K 38/28* | (2006.01) | |
| *A61K 45/06* | (2006.01) | |
| *A61K 31/137* | (2006.01) | |
| *A61K 31/155* | (2006.01) | |
| *A61K 31/198* | (2006.01) | |
| *A61K 31/485* | (2006.01) | |
| *A61K 31/7048* | (2006.01) | |

(52) U.S. Cl.
CPC .......... *C07K 14/605* (2013.01); *A61K 31/137* (2013.01); *A61K 31/155* (2013.01); *A61K 31/198* (2013.01); *A61K 31/485* (2013.01); *A61K 31/7048* (2013.01); *A61K 38/26* (2013.01); *A61K 38/28* (2013.01); *A61K 45/06* (2013.01)

(58) Field of Classification Search
None
See application file for complete search history.

(56) References Cited

U.S. PATENT DOCUMENTS

| | | |
|---|---|---|
| 4,288,627 A | 9/1981 | Kubicek |
| 5,118,666 A | 6/1992 | Habener |
| 5,120,712 A | 6/1992 | Habener |
| 5,424,286 A | 6/1995 | Eng |
| 5,512,549 A | 4/1996 | Chen et al. |
| 5,523,449 A | 6/1996 | Prasad et al. |
| 5,545,618 A | 8/1996 | Buckley et al. |
| 5,614,492 A | 3/1997 | Habener |
| 5,631,224 A | 5/1997 | Efendic et al. |
| 5,670,360 A | 9/1997 | Thorens |
| 5,795,861 A | 8/1998 | Kolterman et al. |
| 5,846,747 A | 12/1998 | Thorens et al. |
| 5,846,937 A | 12/1998 | Drucker |
| 6,006,753 A | 12/1999 | Efendic |
| 6,051,689 A | 4/2000 | Thorens |
| 6,110,703 A | 8/2000 | Egel-Mitani et al. |
| 6,114,304 A | 9/2000 | Kolterman et al. |
| 6,136,784 A | 10/2000 | L'Italien et al. |
| 6,191,102 B1 | 2/2001 | DiMarchi et al. |
| 6,268,343 B1 | 7/2001 | Knudsen et al. |
| 6,271,241 B1 | 8/2001 | DeSimone et al. |
| 6,277,819 B1 | 8/2001 | Efendic |
| 6,284,725 B1 | 9/2001 | Coolidge et al. |
| 6,329,336 B1 | 12/2001 | Bridon et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,410,508 B1 | 6/2002 | Isales et al. |
| 6,410,511 B2 | 6/2002 | L'Italien et al. |
| 6,451,974 B1 | 9/2002 | Hansen |
| 6,458,924 B2 | 10/2002 | Knudsen et al. |
| 6,506,724 B1 | 1/2003 | Hiles et al. |
| 6,528,486 B1 | 3/2003 | Larsen et al. |
| 6,703,359 B1 | 3/2004 | Young et al. |
| 6,767,887 B1 | 7/2004 | Hoffmann et al. |
| 6,858,576 B1 | 2/2005 | Young et al. |
| 6,872,700 B1 | 3/2005 | Young et al. |
| 6,902,744 B1 | 6/2005 | Kolterman et al. |
| 6,924,264 B1 | 8/2005 | Prickett et al. |
| 6,956,026 B2 | 10/2005 | Beeley et al. |

(Continued)

FOREIGN PATENT DOCUMENTS

| | | |
|---|---|---|
| AU | 3247799 A | 9/1999 |
| AU | 2008326324 A1 | 5/2009 |

(Continued)

OTHER PUBLICATIONS

U.S. Appl. No. 14/843,047, filed May 5, 2016, Zealand Pharma A/S.
U.S. Appl. No. 60/132,018, Prickett et al.
U.S. Appl. No. 61/784,294, Tolborg et al.
Abbrecht et al., "Erythrocyte life-span in mice acclimatized to different degrees of hypoxia," J Appl Physiol. 32(4):443-445 (1972).
Action Closing Prosecution in Inter Partes Reexam 95/000,276, mailed Mar. 17, 2011 (25 pages).
Adelhorst et al., "Structure-activity studies of glucagon-like peptide-1," J Biol Chem 269(9):6275-6278 (1994).
Ali et al., "Cardiomyocyte glucagon receptor signaling modulates outcomes in mice with experimental myocardial infarction," Mol Metab. 4(2):132-143 (2015).

(Continued)

*Primary Examiner* — Thomas S Heard
(74) *Attorney, Agent, or Firm* — Clark & Elbing LLP

(57) ABSTRACT

The invention provides materials and methods for the treatment of obesity and excess weight, diabetes, and other associated metabolic disorders. In particular, the invention provides novel acylated glucagon analogue peptides effective in such methods. The peptides may mediate their effect by having increased selectivity for the GLP-1 receptor as compared to human glucagon.

21 Claims, No Drawings
Specification includes a Sequence Listing.

(56) References Cited

U.S. PATENT DOCUMENTS

| | | |
|---|---|---|
| 6,989,366 B2 | 1/2006 | Beeley et al. |
| 7,056,734 B1 | 6/2006 | Egan et al. |
| 7,115,569 B2 | 10/2006 | Beeley et al. |
| 7,138,375 B2 | 11/2006 | Beeley et al. |
| 7,153,825 B2 | 12/2006 | Young et al. |
| 7,157,555 B1 | 1/2007 | Beeley et al. |
| 7,220,721 B1 | 5/2007 | Beeley et al. |
| 7,223,725 B1 | 5/2007 | Beeley et al. |
| 7,226,990 B2 | 6/2007 | Knudsen et al. |
| 7,235,627 B2 | 6/2007 | Knudson et al. |
| 7,297,761 B2 | 11/2007 | Beeley et al. |
| 7,348,404 B2 | 3/2008 | Holm et al. |
| 7,399,489 B2 | 7/2008 | Kolterman et al. |
| 7,407,932 B2 | 8/2008 | Young et al. |
| 7,419,952 B2 | 9/2008 | Beeley et al. |
| 7,442,680 B2 | 10/2008 | Young et al. |
| 7,452,858 B2 | 11/2008 | Hiles et al. |
| 7,521,423 B2 | 4/2009 | Young et al. |
| 7,544,657 B2 | 6/2009 | Ebbehoj et al. |
| 7,601,691 B2 | 10/2009 | Bridon et al. |
| 7,608,692 B2 | 10/2009 | Prickett et al. |
| 7,623,530 B2 | 11/2009 | Hurtta |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,741,269 B2 | 6/2010 | Young et al. |
| 7,858,740 B2 | 12/2010 | Beeley et al. |
| 7,928,065 B2 | 4/2011 | Young et al. |
| 7,935,786 B2 | 5/2011 | Larsen |
| 7,994,122 B2 | 8/2011 | Riber et al. |
| 8,026,210 B2 | 9/2011 | Young et al. |
| 8,057,822 B2 | 11/2011 | Prickett et al. |
| 8,097,698 B2 | 1/2012 | Knudsen et al. |
| 8,263,550 B2 | 9/2012 | Beeley et al. |
| 8,288,338 B2 | 10/2012 | Young et al. |
| 8,445,647 B2 | 5/2013 | Prickett et al. |
| 8,642,540 B2 | 2/2014 | Meier et al. |
| 8,642,541 B2 | 2/2014 | Meier et al. |
| 8,642,727 B2 | 2/2014 | Larsen et al. |
| 8,680,049 B2 | 3/2014 | Meier et al. |
| 8,685,919 B2 | 4/2014 | Meier et al. |
| 9,089,538 B2 | 7/2015 | Neerup et al. |
| 9,156,901 B2 | 10/2015 | Riber et al. |
| 9,169,310 B2 | 10/2015 | Riber et al. |
| 9,180,169 B2 * | 11/2015 | Tolborg .............. A61K 38/26 |
| 9,403,894 B2 | 8/2016 | Meier et al. |
| 9,453,064 B2 | 9/2016 | Just et al. |
| 9,649,362 B2 | 5/2017 | Neerup et al. |
| 9,896,495 B2 | 2/2018 | Riber et al. |
| 9,969,787 B2 | 5/2018 | Just et al. |
| 9,975,939 B2 | 5/2018 | Tolborg et al. |
| 9,988,429 B2 | 6/2018 | Riber et al. |
| 10,004,786 B2 | 6/2018 | Riber et al. |
| 10,093,713 B2 | 10/2018 | Shelton et al. |
| 10,100,097 B2 | 10/2018 | Just et al. |
| 2002/0137666 A1 | 9/2002 | Beeley et al. |
| 2004/0106547 A1 | 6/2004 | Larsen et al. |
| 2005/0070469 A1 | 3/2005 | Bloom et al. |
| 2006/0057137 A1 | 3/2006 | Steiness |
| 2006/0194719 A1 | 8/2006 | Ebbehoj et al. |
| 2006/0293232 A1 | 12/2006 | Levy et al. |
| 2007/111940 A1 | 5/2007 | Larsen et al. |
| 2009/0088369 A1 | 4/2009 | Steiness |
| 2010/0099601 A1 | 4/2010 | Weiss |
| 2010/0190701 A1 | 7/2010 | Day et al. |
| 2010/0240883 A1 | 9/2010 | Wu et al. |
| 2011/0144008 A1 | 6/2011 | Larsen et al. |
| 2011/0230397 A1 | 9/2011 | Carriero et al. |
| 2011/0245165 A1 | 10/2011 | Larsen et al. |
| 2011/0286981 A1 | 11/2011 | Meier et al. |
| 2011/0286982 A1 | 11/2011 | Meier et al. |
| 2011/0293586 A1 | 12/2011 | Meier et al. |
| 2011/0293587 A1 | 12/2011 | Meier et al. |
| 2011/0312878 A1 | 12/2011 | Larsen |
| 2012/0178670 A1 | 7/2012 | Riber et al. |
| 2013/0053304 A1 | 2/2013 | Wang et al. |
| 2013/0064822 A1 | 3/2013 | Ye et al. |
| 2013/0157929 A1 | 6/2013 | Riber et al. |
| 2013/0157935 A1 | 6/2013 | Meier et al. |
| 2013/0157953 A1 | 6/2013 | Petersen et al. |
| 2013/0316941 A1 | 11/2013 | Hamprecht et al. |
| 2014/0011733 A1 | 1/2014 | Fosgerau et al. |
| 2014/0080757 A1 | 3/2014 | Tolborg et al. |
| 2014/0127174 A1 | 5/2014 | Meier et al. |
| 2014/0127175 A1 | 5/2014 | Meier et al. |
| 2014/0187483 A1 | 7/2014 | Steiness |
| 2014/0336356 A1 | 11/2014 | Larsen et al. |
| 2015/0080295 A1 | 3/2015 | Meier et al. |
| 2015/0111817 A1 | 4/2015 | Riber et al. |
| 2015/0111826 A1 | 4/2015 | Riber et al. |
| 2015/0210744 A1 | 7/2015 | Riber et al. |
| 2015/0299281 A1 | 10/2015 | Just et al. |
| 2015/0322130 A1 | 11/2015 | DiMarchi et al. |
| 2015/0376257 A1 | 12/2015 | Riber et al. |
| 2016/0000883 A1 | 1/2016 | Fosgerau et al. |
| 2016/0009777 A1 | 1/2016 | Tolborg et al. |
| 2016/0120951 A1 | 5/2016 | Riber et al. |
| 2016/0304576 A1 | 10/2016 | Meier et al. |
| 2016/0347813 A1 | 12/2016 | Hamprecht et al. |
| 2018/0141990 A1 | 5/2018 | Riber et al. |

FOREIGN PATENT DOCUMENTS

| | | |
|---|---|---|
| CN | 101519446 A | 9/2009 |
| DE | 102008003566 A1 | 7/2009 |
| DE | 102008003568 A1 | 7/2009 |
| EP | 0082731 A1 | 6/1983 |
| EP | 1076066 A1 | 2/2001 |
| EP | 1196444 B1 | 6/2003 |
| EP | 1329458 A2 | 7/2003 |
| EP | 1421950 A1 | 5/2004 |
| EP | 2025684 A1 | 2/2009 |
| EP | 2028192 A1 | 2/2009 |
| EP | 1525219 B1 | 5/2009 |
| EP | 2112161 A2 | 10/2009 |
| JP | 2011-524418 A | 9/2011 |
| JP | 2012-511900 A | 5/2012 |
| WO | WO-91/11457 A1 | 8/1991 |
| WO | WO-91/17243 A1 | 11/1991 |
| WO | WO-93/18786 A1 | 9/1993 |
| WO | WO-95/05848 A1 | 3/1995 |
| WO | WO-97/46584 A1 | 12/1997 |
| WO | WO-98/05351 A1 | 2/1998 |
| WO | WO-98/08531 A1 | 3/1998 |
| WO | WO-98/08871 A1 | 3/1998 |
| WO | WO-98/08873 A1 | 3/1998 |
| WO | WO-98/11125 A1 | 3/1998 |
| WO | WO-98/11126 A1 | 3/1998 |
| WO | WO-98/19698 A1 | 5/1998 |
| WO | WO-98/22577 A1 | 5/1998 |
| WO | WO-98/30231 A1 | 7/1998 |
| WO | WO-98/35033 A1 | 8/1998 |
| WO | WO-98/39022 A1 | 9/1998 |
| WO | WO-98/50351 A1 | 11/1998 |
| WO | WO-99/07404 A1 | 2/1999 |
| WO | WO-99/25727 A2 | 5/1999 |
| WO | WO-99/25728 A1 | 5/1999 |
| WO | WO-99/40788 A1 | 8/1999 |
| WO | WO-99/43707 A1 | 9/1999 |
| WO | WO-99/43708 A1 | 9/1999 |
| WO | WO-99/46283 A1 | 9/1999 |
| WO | WO-99/49788 A1 | 10/1999 |
| WO | WO-99/64060 A1 | 12/1999 |
| WO | WO-00/09666 A2 | 2/2000 |
| WO | WO-00/34331 A2 | 6/2000 |
| WO | WO-00/41546 A2 | 7/2000 |
| WO | WO-00/41548 A2 | 7/2000 |
| WO | WO-00/55119 A1 | 9/2000 |
| WO | WO-00/55184 A1 | 9/2000 |
| WO | WO-00/66629 A1 | 11/2000 |
| WO | WO-00/73331 A2 | 12/2000 |
| WO | WO-01/04156 A1 | 1/2001 |
| WO | WO-01/32158 A2 | 5/2001 |

(56) References Cited

FOREIGN PATENT DOCUMENTS

| | | |
|---|---|---|
| WO | WO-02/34285 A2 | 5/2002 |
| WO | WO-03/022304 A1 | 3/2003 |
| WO | WO-03/053339 A2 | 7/2003 |
| WO | WO-03/053460 A1 | 7/2003 |
| WO | WO-2004/005342 A1 | 1/2004 |
| WO | WO-2004/062685 A2 | 7/2004 |
| WO | WO-2004/096854 A2 | 11/2004 |
| WO | WO-2005/072045 A2 | 8/2005 |
| WO | WO-2006/051110 A2 | 5/2006 |
| WO | WO-2006/097537 A2 | 9/2006 |
| WO | WO-2006/121860 A2 | 11/2006 |
| WO | WO-2006/134340 A2 | 12/2006 |
| WO | WO-2007/024899 A2 | 3/2007 |
| WO | WO-2007/056362 A2 | 5/2007 |
| WO | WO-2007/081824 A2 | 7/2007 |
| WO | WO-2007/095737 A1 | 8/2007 |
| WO | WO-2007/100535 A2 | 9/2007 |
| WO | WO-2008/010101 A2 | 1/2008 |
| WO | WO-2008/071010 A1 | 6/2008 |
| WO | WO-2008/071972 A1 | 6/2008 |
| WO | WO-2008/086086 A2 | 7/2008 |
| WO | WO-2008/101017 A2 | 8/2008 |
| WO | WO-2008/152403 A1 | 12/2008 |
| WO | WO-2008/155257 A1 | 12/2008 |
| WO | WO-2009/067636 A2 | 5/2009 |
| WO | WO-2009/077737 A2 | 6/2009 |
| WO | WO-2009/087081 A2 | 7/2009 |
| WO | WO-2009/087082 A2 | 7/2009 |
| WO | WO-2009/129250 A2 | 10/2009 |
| WO | WO-2009/132129 A2 | 10/2009 |
| WO | WO-2009/152128 A1 | 12/2009 |
| WO | WO-2009/155257 A1 | 12/2009 |
| WO | WO-2009/155258 A2 | 12/2009 |
| WO | WO-2010/002283 A9 | 1/2010 |
| WO | WO-2010/011439 A2 | 1/2010 |
| WO | WO-2010/014946 A2 | 2/2010 |
| WO | WO-2010/016940 A2 | 2/2010 |
| WO | WO-2010/029159 A1 | 3/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/080606 A1 | 7/2010 |
| WO | WO-2010/080609 A1 | 7/2010 |
| WO | WO-2010/096052 A1 | 8/2010 |
| WO | WO-2010/148089 A1 | 12/2010 |
| WO | WO-2011/006497 A1 | 1/2011 |
| WO | WO-2011/080103 A1 | 7/2011 |
| WO | WO-2011/084808 A2 | 7/2011 |
| WO | WO-2011/088837 A1 | 7/2011 |
| WO | WO-2011/094337 A1 | 8/2011 |
| WO | WO-2011/117416 A1 | 9/2011 |
| WO | WO-2011/117417 A1 | 9/2011 |
| WO | WO-2011/119657 A1 | 9/2011 |
| WO | WO-2011/134471 A1 | 11/2011 |
| WO | WO-2011/160630 A2 | 12/2011 |
| WO | WO-2011/160633 A1 | 12/2011 |
| WO | WO-2012/062803 A1 | 5/2012 |
| WO | WO-2012/062804 A1 | 5/2012 |
| WO | WO-2012/098462 A1 | 7/2012 |
| WO | WO-2012/130866 A1 | 10/2012 |
| WO | WO-2012/140117 A1 | 10/2012 |
| WO | WO-2012/150503 A2 | 11/2012 |
| WO | WO-2012/153196 A2 | 11/2012 |
| WO | WO-2012/167744 A1 | 12/2012 |
| WO | WO-2013/041678 A1 | 3/2013 |
| WO | WO-2013/092703 A2 | 6/2013 |
| WO | WO-2013/164483 A1 | 11/2013 |
| WO | WO-2014/016300 A1 | 1/2014 |
| WO | WO-2014/041195 A1 | 3/2014 |
| WO | WO-2015/067715 A2 | 5/2015 |
| WO | WO-2015/124612 A1 | 8/2015 |
| WO | WO-2016/166289 A1 | 10/2016 |

OTHER PUBLICATIONS

Ally et al., "Rapid determination of creatine, phosphocreatine, purine bases and nucleotides (ATP, ADP, AMP, GTP, GDP) in heart biopsies by gradient ion-pair reversed-phase liquid chromatography," J Chromatogr. 575(1):19-27 (1992).

Altschul et al., "Local alignment statistics," Methods Enzymol. 266:460-480 (1996).

Arnold, "Heart failure," <http://www.merckmanuals.com/home/heart_and_blood_vessel_disorders/heart_failure/heart_failure.html?qt=congestive heart failure&alt=sh>, retrieved on Feb. 8, 2015 (12 pages).

Authier et al., "Endosomal proteolysis of glucagon at neutral pH generates the bioactive degradation product miniglucagon-(19-29)," Endocrinology. 144(12):5353-5364 (2003).

Bailey et al., "Glucagon-like peptide-1 and the entero-insular axis in obese hyperglycaemic (ob/ob) mice," Life Sci. 40(6):521-525 (1987).

Ban et al., "Cardioprotective and vasodilatory actions of glucagon-like peptide 1 receptor are mediated through both glucagon-like peptide 1 receptor-dependent and -independent pathways," Circulation. 117(18):2340-2350 (2008).

Bedford et al., "Amino acid structure and 'difficult sequences' in solid phase peptide synthesis," Int J Peptide Protein Res. 40(3-4):300-7 (1992).

Behme et al., "Glucagon-like peptide 1 improved glycemic control in Type 1 diabetes," BMC Endocr Disord. 3(1):3 (2003) (9 pages).

Bell, "Heart failure: the frequent, forgotten, and often fatal complication of diabetes," Diabetes Care. 26(8):2433-41 (2003).

Blache et al., "Endopeptidase from rat liver membranes, which generates miniglucagon from glucagon," J Biol Chem. 268(29):21748-21753 (1993).

Burcelin et al., "Long-lasting antidiabetic effect of a dipeptidyl peptidase IV-resistant analog of glucagon-like peptide-1," Metabolism. 48(2):252-258 (1999).

Buse et al., "The effect of epinephrine, glucagon, and the nutritional state on the oxidation of branched chain amino acids and pyruvate by isolated hearts and diaphragms of the rat," J Biol Chem. 248(2):697-706 (1973).

Buse, "Progressive use of medical therapies in type 2 diabetes," Diabetes Spectrum. 13(4):211-20 (2000).

Byrne et al., "Inhibitory effects of hyperglycaemia on fed jejunal motility: potential role of hyperinsulinaemia," Eur J Clin Invest. 28(1):72-78 (1998).

Carpenter et al., "Rational design of stable lyophilized protein formulations: some practical advice," Pharm Res. 14(8):969-75 (1997).

Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).

Chan et al., "Suppression of weight gain by glucagon in obese Zucker rats," Exp Mol Path. 40(3):320-327 (1984).

Chen et al., "Evidence that the Diabetes gene encodes the leptin receptor: identification of a mutation in the leptin receptor gene in db/db mice," Cell. 84(3):491-5 (1996).

Chen et al., "Tissue-specific expression of unique mRNAs that encode proglucagon-derived peptides or exendin 4 in the lizard," J Biol Chem. 272(7):4108-15 (1997).

Cleland et al., "The development of stable protein formulations: a close look at protein aggregation, deamidation, and oxidation," Crit Rev Ther Drug Carrier Syst. 10(4):307-77 (1993).

Cohen et al., "Oxyntomodulin suppresses appetite and reduces food intake in humans," J Clin Endocrinol Metab. 88(10):4696-4701 (2003).

Coleman, "Effects of parabiosis of obese with diabetes and normal mice," Diabetologia. 9(4):294-8 (1973).

Communication from the European Patent Office for European Patent Application No. 08875673.9, dated Jul. 4, 2012 (6 pages).

D'Alessio et al., "Glucagon-like peptide 1 enhances glucose tolerance both by stimulation of insulin release and by increasing insulin-independent glucose disposal," J Clin Invest. 93(5):2263-66 (1994).

Dakin et al., "Oxyntomodulin inhibits food intake in the rat," Endocrinology. 142(10):4244-4250 (2001).

(56) References Cited

OTHER PUBLICATIONS

Dakin et al., "Peripheral oxyntomodulin reduces food intake and body weight gain in rats," Endocrinology. 145(6):2687-2695 (2004).
Day et al., "A new glucagon and GLP-1 co-agonist eliminates obesity in rodents," Nat Chem Biol. 5(10):749-757 (2009).
De Boer et al., "The tac promoter: a functional hybrid derived from the trp and lac promoters," Proc Natl Acad Sci USA. 80(1):21-5 (1983).
Deacon et al., "Dipeptidyl peptidase IV inhibition potentiates the insulinotropic effect of glucagon-like-peptide 1 in the anesthetized pig," Diabetes. 47(5):764-9 (1998).
Deacon et al., "Dipeptidyl peptidase IV resistant analogues of glucagon-like peptide-1 which have extended metabolic stability and improved biological activity," Diabetologia. 41(3):271-8 (1998).
Decision in Inter Partes Reexam for U.S. Appl. No. 95/000,276, mailed Nov. 25, 2013 (29 pages).
Delgado et al., "The uses and properties of PEG-linked proteins," Crit Rev Ther Drug Carrier Syst. 9(3,4):249-304 (1992).
Diamant et al., "Diabetic cardiomyopathy in uncomplicated type 2 diabetes is associated with the metabolic syndrome and systemic inflammation," Diabetologia 48(8):1669-70 (2005).
Dickstein et al., "ESC Guidelines for the diagnosis and treatment of acute and chronic heart failure 2008: the Task Force for the diagnosis and treatment of acute and chronic heart failure 2008 of the European Society of Cardiology. Developed in collaboration with the Heart Failure Association of the ESC (HFA) and endorsed by the European Society of Intensive Care Medicine (ESICM)," Eur Heart J. 29(19):2388-442 (2008).
Druce et al., "Investigation of structure-activity relationships of Oxyntomodulin (Oxm) using Oxm analogs," Endocrinology. 150(4):1712-1721 (2009).
Drucker, "Glucagon-like peptides," Diabetes. 47(2):159-69 (1998).
Ebert et al., "Gastric inhibitory polypeptide," Clin Gastroenterol. 9(3):679-98 (1980).
Edvell et al., "Initiation of increased pancreatic islet growth in young normoglycemic mice (Umeå +/?)," Endocrinology. 140(2):778-83 (1999).
Ehrlich, "DNA cloning in Bacillus subtilis," Proc Natl Acad Sci USA. 75(3):1433-6 (1978).
EMEA Humalog Information: European Public Assessment Report (EPAR) and Scientific Discussions, 2006 (11 pages).
Eng et al., "Isolation and characterization of exendin-4, an exendin-3 analogue, from Heloderma suspectum venom. Further evidence for an exendin receptor on dispersed acini from guinea pig pancreas.," J Biol Chem. 267(11):7402-7405 (1992).
England et al., "Glucagon carboxyl-terminal derivatives: Preparation, purification and characterization," Biochemistry. 21(5):940-950 (1982).
European Search Opinion and Extended European Search Report for European Patent Application No. 08016668.9, dated Jan. 27, 2009 (5 pages).
European Search Report for European Patent Application No. 09002937, dated Mar. 15, 2010 (5 pages).
European Search Report for European Patent Application No. 99610043, dated Jan. 18, 2000 (2 pages).
European Search Report from European Patent Application No. 07016032.0, completed Jan. 28, 2008 (8 pages).
Extended European Search Report for European Patent Application No. 11774431.8, dated Sep. 30, 2013 (11 pages).
Fang et al., "Diabetic cardiomyopathy: evidence, mechanisms, and therapeutic implications, " Endocr Rev. 25(4):543-67 (2004).
Farah et al., "Studies on the pharmacology of glucagon," J Pharmacol Exp Ther. 129:49-55 (1960).
Finan et al., "Reappraisal of GIP Pharmacology for Metabolic Diseases," Trends Mol Med. 22(5):359-76 (2016).
Fineman et al., Abstract 343-OR: "AC2993 (Synthetic Exendin-4) added to existing metformin (Met) and/or Sulfonylurea (SFU) treatment improved glycemic control in patients with type 2 diabetes (DM2) during 28 days of treatment," Diabetes. 51(Supplement 2):A85, Abstract Book, 62nd Scientific Sessions (2002) (3 pages).
First Examination Report for New Zealand Patent Application No. 702333, dated Jun. 2, 2016 (4 pages).
Francis et al., "PEGylation of cytokines and other therapeutic proteins and peptides: the importance of biological optimisation of coupling techniques," Int J Hematol. 68(1):1-18 (1998).
Frandsen et al., "Glucagon: structure-function relationships investigated by sequence deletions," Hoppe Seylers Z Physiol Chem. 362(6):665-677 (1981).
Gault et al., "Administration of an acylated GLP-1 and GIP preparation provides added beneficial glucose-lowering and insulinotropic actions over single incretins in mice with Type 2 diabetes and obesity," Clin Sci (Lond). 121(3):107-17 (2011).
Gelfanov et al., Discovery and structural optimization of high affinity co-agonists at the glucagon and GLP-1 receptors. Understanding Biology Using Peptides. Sylvie E. Blondelle, 763-764 (2005).
Goldstein et al., "Effects of chronic heart failure on the capacity of glucagon to enhance contractility and adenyl cyclase activity of human papillary muscles," Circulation. 44(4):638-648 (1971).
Gombotz et al. "Biodegradable polymers for protein and peptide drug delivery," Bioconjug Chem. 6(4):332-351 (1995).
Green et al., "Structurally modified analogues of glucagon-like peptide-1 (GLP-1) and glucose-dependent insulinotropic polypeptide (GIP) as future antidiabetic agents," Curr Pharm Des. 10(29):3651-62 (2004).
Greig et al., "Once daily injection of exendin-4 to diabetic mice achieves long-term beneficial effects on blood glucose concentrations," Diabetologia. 42(1):45-50 (1999).
Grieve et al., "Emerging cardiovascular actions of the incretin hormone glucagon-like peptide-1: Potential therapeutic benefits beyond glycaemic control?," Br J Pharmacol. 157(8):1340-51 (2009).
Gunn et al., "Central glucagon-like peptide-I in the control of feeding," Biochem Soc Trans. 24(2):581-4 (1996).
Guo et al., "3'-end-forming signals of yeast mRNA," Mol Cell Biol. 15(11):5983-90 (1995).
Göke et al., "Distribution of GLP-1 binding sites in the rat brain: Evidence that exendin-4 is a ligand of brain GLP-1 binding sites," Eur J Neurosci. 7(11):2294-2300 (1995).
Göke et al., "Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-19655 (1993).
Haffner et al., "Intensive lifestyle intervention or metformin on inflammation and coagulation in participants with impaired glucose tolerance," Diabetes. 54(5):1566-72 (2005).
Hamad et al., "Pharmacologic therapy of chronic heart failure," Am J Cardiovasc Drugs. 7(4):235-48 (2007).
Hansson, "Inflammation, atherosclerosis, and coronary artery disease," N Engl J Med. 352(16):1685-95 (2005).
Harikae, "The effects of a behavioral program in the obese NIDDM patients-observations on daily activity, degree of obesity and blood sugar control," Bulletin of the School of Nursing, Yamaguchi Prefectural University 2:1-13/E (1998) (Abstract in English).
Heinrich et al., "Pre-proglucagon messenger ribonucleic acid: nucleotide and encoded amino acid sequences of the rat pancreatic complementary deoxyribonucleic acid," Endocrinology. 115(6):2176-81 (1984).
Hjorth et al., "Glucagon and glucagon-like peptide 1: Selective receptor recognition via distinct peptide epitopes," J Biol Chem. 269(48):30121-30124 (1994).
Holst, "Enteroglucagon," Annu Rev Physiol. 59:257-71 (1997).
Holst, "Glucagon-like peptide-1, a gastrointestinal hormone with a pharmaceutical potential," Curr Med Chem. 6(11):1005-17 (1999).
Holst, "The physiology of glucagon-like peptide 1," Physiol Rev. 87(4): 1409-39 (2007).
Hostrup et al., Modification of Peptides and Proteins. Delivery Technologies for Biopharmaceuticals: Peptides, Proteins, Nucleic Acids and Vaccines. Jorgensen, Nielsen, 171-91 (2009).

(56) References Cited

OTHER PUBLICATIONS

Hruby et al., "The design and biological activities of glucagon agonists and antagonists, and their use in examining the mechanisms of glucose action," Curr Med Chem—Imm, Endoc Metab Agents. 1(3):199-215 (2001).
Hudecz et al., "Synthesis, conformation, biodistribution, and in vitro cytotoxicity of daunomycin-branched polypeptide conjugates," Bioconjug Chem. 3(1):49-57 (1992).
Hui et al., "The short half-life of glucagon-like peptide-1 in plasma does not reflect its long-lasting beneficial effects," Eur J Endocrinol. 146(6):863-9 (2002).
Ingwall et al., "Is the failing heart energy starved? On using chemical energy to support cardiac function," Circ Res. 95(2):135-45 (2004).
International Preliminary Examination Report for International Application No. PCT/DK03/00463, dated Sep. 20, 2004 (5 pages).
International Preliminary Report on Patentability for PCT/EP2013/069286, completed Jan. 19, 2015 (40 pages).
International Preliminary Report on Patentability for PCT/GB2008/002041, dated Dec. 17, 2009 (7 pages).
International Search Report and Written Opinion for International Application No. PCT/IB2012/001090, dated Jan. 25, 2013 (15 pages).
International Search Report and Written Opinion for International Patent Application No. PCT/EP2012/071766, dated Feb. 15, 2013 (9 pages).
International Search Report and Written Opinion for PCT/EP2013/059319, dated Sep. 12, 2013 (12 pages).
International Search Report and Written Opinion for PCT/EP2013/065519, dated Dec. 6, 2013 (11 pages).
International Search Report and Written Opinion for PCT/EP2013/069286, dated Dec. 18, 2013 (16 pages).
International Search Report and Written Opinion for PCT/GB2008/004121, dated Jun. 30, 2009 (25 pages).
International Search Report and Written Opinion for PCT/GB2008/004130, dated Mar. 25, 2009 (17 pages).
International Search Report and Written Opinion for PCT/GB2008/004132, dated Jun. 10, 2009 (16 pages).
International Search Report for International Application No. PCT/DK00/00393, dated Nov. 8, 2000 (3 pages).
International Search Report for International Application No. PCT/DK03/00463, dated Oct. 22, 2003 (7 pages).
International Search Report for International Application No. PCT/DK2010/000099, dated Dec. 2, 2010 (2 pages).
International Search Report for International Application No. PCT/DK2011/000067, dated Dec. 9, 2011 (4 pages).
International Search Report for International Application No. PCT/DK2011/050133 dated Oct. 6, 2011 (5 pages).
International Search Report for International Application No. PCT/IB2012/000134, dated Jun. 25, 2012 (3 pages).
International Search Report for International Application No. PCT/DK2011/050018, dated May 30, 2011 (6 pages).
International Search Report for PCT/DK2011/000072, dated Dec. 6, 2011 (3 pages).
International Search Report for PCT/GB2008/002041, dated Sep. 9, 2008 (3 pages).
International Search Report for PCT/GB2008/004157, dated Jun. 4, 2009 (21 pages).
Irwin et al., "Antidiabetic potential of two novel fatty acid derivatised, N-terminally modified analogues of glucose-dependent insulinotropic polypeptide (GIP): N—AcGIP(LysPAL16) and N—AcGIP(LysPAL37)," Biol Chem. 386(7):679-87 (2005).
Irwin et al., "GIP(Lys16PAL) and GIP(Lys37PAL): novel long-acting acylated analogues of glucose-dependent insulinotropic polypeptide with improved antidiabetic potential," J Med Chem. 49(3):1047-54 (2006).
Jaya et al., "Mechanism of hypocholesterolemic action of glucagon," J Biosci. 12(2):111-4 (1987).
Jessup et al., "2009 focused update: ACCF/AHA Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation.," Circulation. 119(14):1977-2016 (2009).
Joshi et al., "The estimation of glutaminyl deamidation and aspartyl cleavage rates in glucagon," Int J Pharm. 273(1-2):213-219 (2004).
Juntti-Berggren et al., "The antidiabetogenic effect of GLP-1 is maintained during a 7-day treatment period and improves diabetic dyslipoproteinemia in NIDDM patients," Diabetes Care. 19(11):1200-6 (1996).
Kallenbach et al., Role of the peptide bond in protein structure and folding. The Amide Linkage: Selected Structural Aspects in Chemistry, Biochemistry, and Materials Science. Greenberg, Breneman, Liebman, 599-625 (2000).
Knudsen et al., "Potent derivatives of glucagon-like peptide-1 with pharmacokinetic properties suitable for once daily administration," J Med Chem. 43(9):1664-1669 (2000).
Korc, "Islet growth factors: curing diabetes and preventing chronic pancreatitis?," J Clin Invest. 92(3):1113-4 (1993).
Krchnák et al., "Aggregation of resin-bound peptides during solid-phase peptide synthesis. Prediction of difficult sequences," Int J Pept Protein Res. 42(5):450-4 (1993).
Larsen et al., "Sequence-assisted peptide synthesis (SAPS)," J Peptide Res. 52(6):470-6 (1998).
Lefébvre, "The intriguing diversity of the glucagon gene products," Curr Diab Rep. 2(3):201-2 (2002).
Leiter et al., "Influence of dietary carbohydrate on the induction of diabetes in C57BL/KsJ-db/db diabetes mice," J Nutr. 113(1):184-95 (1983).
Levey et al., "Activation of adenyl cyclase by glucagon in cat and human heart," Circ Res. 24(2):151-6 (1969).
Lopaschuk et al., "Measurements of fatty acid and carbohydrate metabolism in the isolated working rat heart," Mol Cell Biochem. 172(1-2):137-47 (1997).
Loyter et al., "Mechanisms of DNA uptake by mammalian cells: fate of exogenously added DNA monitored by the use of fluorescent dyes," Proc Natl Acad Sci USA. 79(2):422-6 (1982).
Lvoff et al., "Glucagon in heart failure and in cardiogenic shock. Experience in 50 patients," Circulation. 45(3):534-42 (1972).
López-Delgado et al., "Effects of glucagon-like peptide 1 on the kinetics of glycogen synthase a in hepatocytes from normal and diabetic rats," Endocrinology. 139(6):2811-17 (1998).
Madsen et al., "Structure-activity and protraction relationship of long-acting glucagon-like peptide-1 derivatives: importance of fatty acid length, polarity, and bulkiness," J Med Chem. 50(24):6126-32 (2007).
Malde et al., "Understanding interactions of gastric inhibitory polypeptide (GIP) with its G-protein coupled receptor through NMR and molecular modeling," J Pept Sci. 13(5):287-300 (2007).
Manhart et al., "Structure-function analysis of a series of novel GIP analogues containing different helical length linkers," Biochemistry. 42(10):3081-8 (2003).
Manning et al., "Stability of protein pharmaceuticals," Pharm Res. 6(11):903-18 (1989).
Matsumoto et al., "Plasma Incretin Levels and Dipeptidyl Peptidase-4 Activity in Patients with Obstructive Sleep Apnea," Ann Am Thorac Soc. 13(8):1378-87 (2016).
Matthes et al., "Simultaneous rapid chemical synthesis of over one hundred oligonucleotides on a microscale," EMBO J. 3(4):801-5 (1984).
Mayer et al., "Effect of glucagon on cyclic 3',5'-AMP, phosphorylase activity and contractility of heart muscle of the rat," Circ Res. 26(2):225-33 (1970).
McKee et al., "Receptor binding and adenylate cyclase activities of glucagon analogues modified in the N-terminal region," Biochemistry. 25(7):1650-1656 (1986).
Mehta, "Diabetic cardiomyopathy: insights into pathogenesis, diagnostic challenges, and therapeutic options," Intl J Pharm Sci Res. 3(10):3565-3576 (2012).
Meurer et al., "Properties of native and in vitro glycosylated forms of the glucagon-like peptide-1 receptor antagonist exendin (9-39)," Metabolism. 48(6):716-24 (1999).

(56) References Cited

OTHER PUBLICATIONS

Meyer et al., Effects of conformation on the Chemical Stability of Pharmaceutically Relevant Polypeptides. *Rational design of stable protein formulations*. Carpenter and Manning, 85-6 (2002).
Mojsov, "Structural requirements for biological activity of glucagon-like peptide-I," Int J Pept Protein Res. 40(3-4):333-43 (1992).
Nauck et al., "Glucagon-like peptide 1 and its potential in the treatment of non-insulin-dependent diabetes mellitus," Horm Metab Res. 29(9):411-6 (1997).
Navarro et al., "Colocalization of glucagon-like peptide-1 (GLP-1) receptors, glucose transporter GLUT-2, and glucokinase mRNAs in rat hypothalamic cells: evidence for a role of GLP-1 receptor agonists as an inhibitory signal for food and water intake," J Neurochem 67(5):1982-91 (1996).
NCBI Blast for Accession No. 721913A, retrieved on Dec. 15, 2009 (1 page).
Neubauer et al., "Myocardial phosphocreatine-to-ATP ratio is a predictor of mortality in patients with dilated cardiomyopathy," Circulation. 96(7):2190-6 (1997) (9 pages).
Neumann et al., "Gene transfer into mouse lyoma cells by electroporation in high electric fields," EMBO J. 1(7):841-5 (1982).
Nikolaidis et al., "Active metabolite of GLP-1 mediates myocardial glucose uptake and improves left ventricular performance in conscious dogs with dilated cardiomyopathy," Am J Physiol Heart Circ Physiol. 289(6):H2401-8 (2005).
Nikolaidis et al., "Recombinant glucagon-like peptide-1 increases myocardial glucose uptake and improves left ventricular performance in conscious dogs with pacing-induced dilated cardiomyopathy," Circulation. 110(8):955-61 (2004).
Notice of Allowance and Allowed Claims for U.S. Appl. No. 13/383,783, dated Jun. 22, 2015 (5 pages).
Notice of Allowance, previously Allowed Claims and Amendment after Allowance for U.S. Appl. No. 13/704,299, dated Jun. 26, 2015 (15 pages).
Notice of Allowance, previously Allowed Claims and Amendment after Allowance for U.S. Appl. No. 14/029,529, dated Jun. 29, 2015 (14 pages).
Notice of Opposition to a European Patent for European Patent No. 1525219 on behalf of Novo Nordisk A/S, dated Feb. 25, 2010 (24 pages).
Orskov, "Glucagon-like peptide-1, a new hormone of the entero-insular axis," Diabetologia. 35(8):701-11 (1992).
Overgaard et al., "Inotropes and vasopressors: review of physiology and clinical use in cardiovascular disease," Circulation. 118(10):1047-56 (2008).
Owens et al., "Insulins today and beyond," Lancet. 358(9283):739-46 (2001).
Pan et al., "Design of a long acting peptide functioning as both a glucagon-like peptide-1 receptor agonist and a glucagon receptor antagonist," J Biol Chem. 281(18):12506-12515 (2006).
Parkes et al., "Insulinotropic actions of exendin-4 and glucagon-like peptide-1 in vivo and in vitro," Metabolism. 50(5):583-9 (2001).
Parlevliet et al., "CNTO736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Parlevliet et al., "Oxyntomodulin ameliorates glucose intolerance in mice fed a high-fat diet," Am J Physiol Endocrinol Metab. 294(1):E142-E147 (2008).
Partial European Search Report for European Patent Application No. 03005786, dated Oct. 23, 2003 (6 pages).
Partial European Search Report for European Patent Application No. 99610043, dated Jan. 18, 2000 (4 pages).
Pederson et al., "Improved glucose tolerance in Zucker Fatty Rats by oral administration of the dipeptidyl peptidase IV inhibitor isoleucine thiazolidide," Diabetes. 47(8):1253-8 (1998).
Petersen et al., "ZP10—A new GLP-1 agonist that prevents diabetes progression and increases insulin mRNA expression in db/db mice," 38th Annual Meeting of the European Association for the Study of Diabetes (EASD). Budapest, Hungary, Sep. 1-5, 2002, *Diabetologia* 45 (Suppl. 1):A147, Abstract No. 447 (2002) (2 pages).
Pocai et al., "Glucagon-like peptide 1/glucagon receptor dual agonism reverses obesity in mice," Diabetes. 58(10):2258-66 (2009).
Pocai, "Glucagon signaling in the heart: activation or inhibition?," Mol Metab. 4(2):81-2 (2015).
Pohl et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J Biol Chem. 273(16):9778-84 (1998).
Poon et al., "Exenatide improves glycemic control and reduces body weight in subjects with type 2 diabetes: a dose-ranging study," Diabetes Technol Ther. 7(3):467-77 (2005).
Pratesi et al., "Poly-L-aspartic acid as a carrier for doxorubicin: a comparative in vivo study of free and polymer-bound drug," Br J Cancer. 52(6):841-848 (1985).
Pridal et al., "Absorption of glucagon-like peptide-1 can be protracted by zinc or protamine," Int J Pharm 136:53-59 (1996).
Protest of U.S. Appl. No. 12/664,534 Pursuant 37 CFR 1.291, dated Jan. 13, 2010 (14 pages).
Raufman et al., "Exendin-3, a novel peptide from Heloderma horridum venom, interacts with vasoactive intestinal peptide receptors and a newly described receptor on dispersed acini from guinea pig pancreas. Description of exendin-3(9-39) amide, a specific exendin receptor antagonist," J Biol Chem. 266(5):2897-902 (1991).
Raufman et al., "Truncated glucagon-like peptide-1 interacts with exendin receptors on dispersed acini from guinea pig pancreas. Identification of a mammalian analogue of the reptilian peptide exendin-4," J Biol Chem. 267(30):21432-7 (1992).
Raufman, "Bioactive peptides from lizard venoms," Regul Pept. 61(1):1-18 (1996).
Ritzel et al., "A synthetic glucagon-like peptide-1 analog with improved plasma stability," J Endocrinol. 159(1):93-102 (1998).
Roach et al., "Improved postprandial glycemic control during treatment with humalog Mix25, a novel protamine-based insulin lispro formulation. Humalog Mix25 Study Group," Diabetes Care. 22(8):1258-61 (1999).
Robberecht et al., "Comparative efficacy of seven synthetic glucagon analogs, modified in position 1, 2, and/or 12, on liver and heart adenylate cyclase from rat," Peptides. 7(Suppl 1):109-12 (1986).
Rolin et al., "The long-acting GLP-1 derivative NN2211 ameliorates glycemia and increases beta-cell mass in diabetic mice," Am J Physiol Endocrinol Metab. 283(4):E745-52 (2002).
Rooman et al., "Gastrin stimulates beta-cell neogenesis and increases islet mass from transdifferentiated but not from normal exocrine pancreas tissue," Diabetes. 51(3):686-90 (2002).
Rose et al., "Insulin proteinase liberates from glucagon a fragment known to have enhanced activity against Ca2+ + Mg2+-dependent ATPase," Biochem J. 256(3):847-51 (1988).
Runge et al., "Differential structural properties of GLP-1 and exendin-4 determine their relative affinity for the GLP-1 receptor N-terminal extracellular domain," Biochemistry. 46(19):5830-40 (2007).
Saraceni et al., "Effects of glucagon-like peptide-1 and long-acting analogues on cardiovascular and metabolic function," Drugs R D. 8(3):145-53 (2007).
Sowden et al., "Oxyntomodulin increases intrinsic heart rate in mice independent of the glucagon-like peptide-1 receptor," Am J Physiol Regul lntegr Comp Physiol. 292(2): R962-70 (2007).
Stoffers et al., "Insulinotropic glucagon-like peptide 1 agonists stimulate expression of homeodomain protein IDX-1 and increase islet size in mouse pancreas," Diabetes. 49(5):741-8 (2000).
Suarez-Pinzon et al., "Combination therapy with epidermal growth factor and gastrin increases beta-cell mass and reverses hyperglycemia in diabetic NOD mice," Diabetes. 54(9):2596-601 (2005).
Suarez-Pinzon et al., "Combination therapy with glucagon-like peptide-1 and gastrin restores normoglycemia in diabetic NOD mice," Diabetes. 57(12):3281-8 (2008).
Tang-Christensen et al., "Central administration of GLP-1-(7-36) amide inhibits food and water intake in rats," Am J. Physiol. 271(4 Pt 2):R848-56 (1996).

(56) References Cited

OTHER PUBLICATIONS

Thorkildsen et al., "The exendin analogue ZP10 increases insulin mRNA expression in db/db mice," Nedergaard Symposium, Odense, Denmark, Jan. 24, 2002 (Poster presentation).
Thorkildsen et al., "ZP10—A New GLP-1 agonist that increases insulin mRNA expression," Nedergaard Symposium, Odense, Denmark, Jan. 24, 2002 (abstract only) (1 page).
Thorkildsen et al., "ZP10—A new GLP-1 agonist that prevents diabetes progression and increases insulin mRNA expression in db/db mice," 38th Annual Meeting of the European Associate for the Study of Diabetes (EASD), Budapest, Hungary, Sep. 1-5, 2002, Poster presentation.
Tomita et al., "Pancreatic islets of obese hyperglycemic mice (ob/ob)," Pancreas. 7(3):367-375 (1992).
Tourrel et al., "Persistent improvement of type 2 diabetes in the Goto-Kakizaki Rat model by expansion of the beta-cell mass during the prediabetic period with glucagon-like peptide-1 or exendin-4," Diabetes. 51(5):1443-52 (2002).
Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).
Turton et al., "A role for glucagon-like peptide-1 in the central regulation of feeding," Nature 379(6560):69-72 (1996).
U.S. Appl. No. 14/095,667, filed Dec. 3, 2013 (99 pages).
U.S. Appl. No. 14/116,268, filed Nov. 7, 2013 (164 pages).
U.S. Appl. No. 60/132,018, filed Apr. 30, 1999 (101 pages).
Uesaka et al., "Glucagon-like peptide isolated from the eel intestine: Effects on atrial beating," J Exp Bio. 204(Pt 17):3019-26 (2001).
Underwood et al., "Crystal structure of glucagon-like peptide-1 in complex with the extracellular domain of the glucagon-like peptide-1 receptor," J Biol Chem. 285(1):723-30 (2010).
Unson et al., "Glucagon antagonists: contribution to binding and activity of the amino-terminal sequence 1-5, position 12, and the putative alpha-helical segment 19-27," J Biol Chem. 264(2):789-794 (1989).
Unson et al., "Identification of an essential serine residue in glucagon: implication for an active site triad," Proc Natl Acad Sci USA. 91(2):454-458 (1994).
Unson et al., "Positively charged residues at positions 12, 17, and 18 of glucagon ensure maximum biological potency," J Biol Chem. 273(17):10308-10312 (1998).
Uttenthal et al., "Molecular forms of glucagon-like peptide-1 in human pancreas and glucagonomas," J Clin Endocrinol Metabol. 61(3):472-479 (1985).
Villa-Komaroff et al., "A bacterial clone synthesizing proinsulin," Proc Natl Acad Sci USA. 75(8):3727-31 (1978).
Wang et al., "Glucagon-like peptide-1 treatment delays the onset of diabetes in 8 week-old db/db mice," Diabetologia. 45(9):1263-73 (2002).
Warnica, "Acute coronary syndromes (Heart Attack; Myocardial Infarction; Unstable Angina)," <http://www.merckmanuals.com/home/heart_and_blood_vessel_disorders/coronary_artery_disease/acute_coronary_syndromes_heart_attack_myocardial_infarction_unstable_angina.html?qt=congestive heart failure&alt=sh>, retrieved on Feb. 8, 2015 (8 pages).
Wermuth et al., "Glossary of terms used in medicinal chemistry," Pure & Appl Chem. 70(5):1129-43 (1998).
Wettergren et al., "Truncated GLP-1 (proglucagon 78-107-amide) inhibits gastric and pancreatic functions in man," Dig Dis Sci. 38(4):665-73 (1993).
White, "A review of potential cardiovascular uses of intravenous glucagon administration," J Clin Pharmacol. 39(5):442-7 (1999).
Wiberg et al., "Replication and expression in mammalian cells of transfected DNA; description of an improved erythrocyte ghost fusion technique," Nucleic Acids Res. 11(21):7287-7302 (1983).
Written Opinion for PCT/DK2011/000072, dated Dec. 6, 2011 (6 pages).
Written Opinion for Singapore Application No. 201209089-0, dated Nov. 8, 2013 (10 pages).

Written Opinion of the International Searching Authority for PCT/GB2008/002041, dated Sep. 9, 2008 (6 pages).
Xu et al., "Exendin-4 stimulates both beta-cell replication and neogenesis, resulting in increased beta-cell mass and improved glucose tolerance in diabetic rats," Diabetes. 48(12):2270-6 (1999).
Yabe et al., "Quantitative measurements of cardiac phosphorus metabolites in coronary artery disease by 31P magnetic resonance spectroscopy," Circulation. 92(1):15-23 (1995) (14 pages).
Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes. 48(5):1026-34 (1999).
Young et al., "Physiological and genetic factors affecting transformation of Bacillus subtilis," J Bacteriol. 81:823-9 (1961).
Zalipsky, "Functionalized poly(ethylene glycol) for preparation of biologically relevant conjugates," Bioconjug Chem. 6(2):150-165 (1995).
Zander et al., "Additive glucose-lowering effects of glucagon-like peptide-1 and metformin in type 2 diabetes," Diabetes Care. 24(4):720-5 (2001).
Zhao et al., "Direct effects of glucagon-like peptide-1 on myocardial contractility and glucose uptake in normal and postischemic isolated rat hearts," J Pharmacol Exp Ther. 317(3):1106-13 (2006).
Zhou et al., "Glucagon-like peptide 1 and exendin-4 convert pancreatic AR42J cells into glucagon- and insulin-producing cells," Diabetes. 48(12): 2358-66 (1999).
Zhu et al.,"The role of dipeptidyl peptidase IV in the cleavage of glucagon family peptides: in vivo metabolism of pituitary adenylate cyclase activating polypeptide-(1-38)," J Biol Chem. 278(25):22418-22423 (2003).
Chabenne et al., "Optimization of the native glucagon sequence for medicinal purposes," J Diabetes Sci Technol. 4(6):1322-31 (2010).
Periasamy et al., "Molecular basis of diastolic dysfunction," available in PMC Jul. 6, 2009, published in final edited form as: Heart Fail Clin. 4(1):13-21 (2008) (13 pages).
Yasgur, "Premature ventricle contractions in heart failure: a closer examination," http://www.thecardiologyadvisor.com/heart-failure/premature-ventricle-contractions-in-heart-failure/article/515445/, retrieved Sep. 10, 2017 (3 pages).
Office Action for Colombian Application No. 16089238, dated Sep. 13, 2017 (18 pages).
Bowie et al., "Deciphering the message in protein sequences: tolerance to amino acid substitutions," Science. 247(4948):1306-10 (1990).
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111, 2129-38, 1990.
Bork, "Powers and pitfalls in sequence analysis: the 70% hurdle," Genome Research 10, 398-400, 2000.
Lazar et al., "Transforming growth factor alpha: mutation of aspartic acid 47 and leucine 48 results in different biological activities," Mol. Cell. Biol. 8, 1247-52, 1988.
U.S. Appl. No. 15/852,458, filed Dec. 22, 2017 (54 pages).
Sturm et al., "Structure-function studies on positions 17, 18, and 21 replacement analogues of glucagon: the importance of charged residues and salt bridges in glucagon biological activity," J Med Chem. 41(15): 2693-700 (1998) (8 pages).
Matsuyama, "Glucagon and diabetes," Shijonawate Gakuen Bulletin of Faculty of Rehabilitation. 7:1-12 (2011) (English Abstract Included).
English Translation of Notice of Reasons for Rejection from Office Action for Japanese Application No. 2015-523532, dated Apr. 24, 2018 (8 pages).
Kawashima et al., "Case of pancreatic diabetes with improvement in carbohydrate and lipid metabolism brought about by injections of a small quantity of glucagon," The Journal of the Japanese Society of Internal Medicine. 88(2):336-8 (1999) (English Abstract Included).

\* cited by examiner

ACYLATED GLUCAGON ANALOGUES

CROSS-REFERENCE TO RELATED APPLICATIONS

This application claims priority to U.S. Provisional No. 61/892,256, filed Oct. 17, 2013, which is hereby incorporated by reference in its entirety.

FIELD OF THE INVENTION

The present invention relates to acylated glucagon analogues and their medical use, for example in the treatment of obesity and excess weight, diabetes, and other metabolic disorders.

BACKGROUND OF THE INVENTION

Pre-proglucagon is a 158 amino acid precursor polypeptide that is differentially processed in the tissues to form a number of structurally related proglucagon-derived peptides, including glucagon (Glu), glucagon-like peptide-1 (GLP-1), glucagon-like peptide-2 (GLP-2), and oxyntomodulin (OXM). These molecules are involved in a wide variety of physiological functions, including glucose homeostasis, insulin secretion, gastric emptying and intestinal growth, as well as regulation of food intake.

Glucagon is a 29-amino acid peptide that corresponds to amino acids 53 to 81 of pre-proglucagon. Oxyntomodulin (OXM) is a 37 amino acid peptide which includes the complete 29 amino acid sequence of glucagon with an octapeptide carboxyterminal extension (amino acids 82 to 89 of pre-proglucagon, and termed "intervening peptide 1" or IP-1. The major biologically active fragment of GLP-1 is produced as a 30-amino acid, C-terminally amidated peptide that corresponds to amino acids 98 to 127 of pre-proglucagon.

Glucagon helps maintain the level of glucose in the blood by binding to glucagon receptors on hepatocytes, causing the liver to release glucose—stored in the form of glycogen—through glycogenolysis. As these stores become depleted, glucagon stimulates the liver to synthesize additional glucose by gluconeogenesis. This glucose is released into the bloodstream, preventing the development of hypoglycemia.

GLP-1 decreases elevated blood glucose levels by improving glucose-stimulated insulin secretion and promotes weight loss chiefly through decreasing food intake.

OXM is released into the blood in response to food ingestion and in proportion to meal calorie content. OXM has been shown to suppress appetite and inhibit food intake in humans (Cohen et al, Journal of Endocrinology and Metabolism, 88, 4696-4701, 2003; WO 2003/022304). In addition to those anorectic effects, which are similar to those of GLP-1, OXM must also affect body weight by another mechanism, since rats treated with oxyntomodulin show less body weight gain than pair-fed rats (Bloom, Endocrinology 2004, 145, 2687). Treatment of obese rodents with OXM also improves their glucose tolerance (Parlevliet et al, Am J Physiol Endocrinol Metab, 294, E142-7, 2008) and suppresses body weight gain (WO 2003/022304).

OXM activates both the glucagon and the GLP-1 receptors with a two-fold higher potency for the glucagon receptor over the GLP-1 receptor, but is less potent than native glucagon and GLP-1 on their respective receptors. Human glucagon is also capable of activating both receptors, though with a strong preference for the glucagon receptor over the GLP-1 receptor. GLP-1 on the other hand is not capable of activating glucagon receptors. The mechanism of action of oxyntomodulin is not well understood. In particular, it is not known whether some of the extrahepatic effects of the hormone are mediated through the GLP-1 and glucagon receptors, or through one or more unidentified receptors.

Other peptides have been shown to bind and activate both the glucagon and the GLP-1 receptor (Hjort et al, Journal of Biological Chemistry, 269, 30121-30124, 1994) and to suppress body weight gain and reduce food intake (see, for example, WO 2006/134340, WO 2007/100535, WO 2008/10101, WO 2008/152403, WO 2009/155257, WO 2009/155258, WO2010/070252, WO2010/070253, WO2010/070255, WO2010/070251, WO2011/006497, WO2011/160630, WO2011/160633, WO2013/092703, WO2014/041195.

Obesity is a globally increasing health problem associated with various diseases, particularly cardiovascular disease (CVD), type 2 diabetes, obstructive sleep apnea, certain types of cancer, and osteoarthritis. As a result, obesity has been found to reduce life expectancy. According to 2005 projections by the World Health Organization there are 400 million adults (age>15) classified as obese worldwide. In the US, obesity is now believed to be the second-leading cause of preventable death after smoking.

The rise in obesity drives an increase in diabetes, and approximately 90% of people with type 2 diabetes may be classified as obese. There are 246 million people worldwide with diabetes, and by 2025 it is estimated that 380 million will have diabetes. Many have additional cardiovascular risk factors, including high/aberrant LDL and triglycerides and low HDL.

SUMMARY OF THE INVENTION

In a first aspect, the invention provides a compound having the formula:

$$R^1-P^1-P^2-R^2$$

wherein $R^1$ is H, $C_{1-4}$ alkyl, acetyl, formyl, benzoyl or trifluoroacetyl;
$R^2$ is OH or $NH_2$;
$P^1$ is a peptide having the sequence:

(SEQ ID NO: 65)
H-X2-X3-GTFTSDYSKYLDS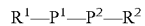AAHDFVEWLLSA wherein:
X2 is selected from Aib, Ala, D-Ala, Ser, N-Me-Ser, Ac3c, Ac4c and Ac5c;
X3 is selected from Gln and His;
$P^2$ is absent or is a sequence of 1-20 amino acid units independently selected from the group consisting of Ala, Leu, Ser, Thr, Tyr, Cys, Glu, Lys, Arg, Dbu, Dpr and Orn; or a pharmaceutically acceptable salt or solvate thereof;
ψ is a residue of Lys, Arg, Orn or Cys in which the side chain is conjugated to a substituent having the formula $-Z^2-Z^1$;
$-Z^1$ is a fatty chain having a polar group at one end of the chain and a connection to $Z^2$, —X— at the end of the chain distal from the polar group,
wherein the polar group comprises a carboxylic acid or a carboxylic acid bioisostere, a phosphonic acid, or a sulfonic acid group;

and —X— is a bond, —CO—, —SO—, or —SO$_2$—;
—Z$^2$— is a spacer of formula:

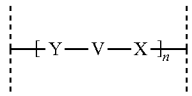

wherein:
each Y is independently —NH, —NR, —S or —O, where R is alkyl, a protecting group or forms a linkage to another part of the spacer Z$^2$;
each X is independently a bond, CO—, SO—, or SO$_2$—;
with the proviso that when Y is —S, X is a bond;
each V is independently a bivalent organic moiety linking Y and X;
and n is 1-10;
or a pharmaceutically acceptable salt or solvate thereof.
P$^1$ may have the sequence:

```
                                    (SEQ ID NO: 66)
H-Aib-QGTFTSDYSKYLDSΨAAHDFVEWLLSA
e.g.
                                    (SEQ ID NO: 67)
H-Aib-QGTFTSDYSKYLDS-K([15-carboxy-pentadecanoyl]-
isoGlu)-AAHDFVEWLLSA.
```

The compound of the invention may be:

```
                                    (SEQ ID NO: 68)
H-H-Aib-QGTFTSDYSKYLDSΨAAHDFVEWLLSA-NH₂
e.g.
                                    (SEQ ID NO: 69)
H-H-Aib-QGTFTSDYSKYLDS-K([15-carboxy-
pentadecanoyl]-isoGlu)-AAHDFVEWLLSA-NH₂.
```

In a second aspect, the invention provides a compound having the formula:

R$^1$—P$^1$—P$^2$—R$^2$ wherein
R$^1$ is H, C$_{1-4}$ alkyl, acetyl, formyl, benzoyl or trifluoroacetyl;
R$^2$ is OH or NH$_2$;
P$^1$ is a peptide having the sequence:

```
                                    (SEQ ID No: 1)
His-X2-X3-GTFTSDYSKYL-X15-X16-X17-X18-A-X20-DFI-
X24-WLE-X28-A
``` wherein:
X2 is selected from Aib, Ac3c, Ac4c and Ac5c;
X3 is selected from Gln and His;
X15 is selected from Asp and Glu;
X16 is selected from Glu and ψ;
X17 is selected from Arg and ψ;
X18 is selected from Ala and Arg;
X20 is selected from Lys and His;
X24 is selected from Glu and ψ;
X28 is selected from Ser and ψ;
and P$^2$ is absent or is a sequence of 1-20 amino acid units independently selected from the group consisting of Ala, Leu, Ser, Thr, Tyr, Cys, Glu, Lys, Arg, Dbu, Dpr and Orn;

wherein the compound contains one and only one ψ
and wherein said ψ is a residue of Lys, Arg, Orn or Cys in which the side chain is conjugated to a substituent having the formula —Z$^2$—Z$^1$;
—Z$^1$ is a fatty chain having a polar group at one end of the chain and a connection to Z$^2$, —X— at the end of the chain distal from the polar group,
wherein the polar group comprises a carboxylic acid or a carboxylic acid bioisostere, a phosphonic acid, or a sulfonic acid group;
and —X— is a bond, —CO—, —SO—, or —SO$_2$—;
—Z$^2$— is a spacer of formula:

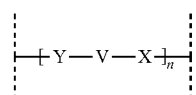

wherein:
each Y is independently —NH, —NR, —S or —O, where R is alkyl, a protecting group or forms a linkage to another part of the spacer Z$^2$;
each X is independently a bond, CO—, SO—, or SO$_2$—;
with the proviso that when Y is —S, X is a bond;
each V is independently a bivalent organic moiety linking Y and X;
and n is 1-10;
or a pharmaceutically acceptable salt or solvate thereof.
In some embodiments of the second aspect:
X2 is selected from Aib and Ac4c;
X3 is Gln;
X15 is selected from Asp and Glu;
X16 is ψ;
X17 is Arg;
X18 is Ala;
X20 is selected from Lys and His;
X24 is Glu;
X28 is Ser.
Useful combinations of residues include the following:
X2 is Ac4c and X20 is Lys;
X2 is Aib and X20 is His.
Additionally or alternatively, it may be desirable that X2 is Aib if X15 is E
or that X15 is D if X2 is Ac4c.
Particularly interesting substituents Z$^2$Z$^1$ include [17-carboxy-heptadecanoyl]-isoGlu-Peg3-Peg3 and [17-carboxy-heptadecanoyl]-isoGlu-GSGSGG (SEQ ID NO: 34).
P$^1$ may have a sequence selected from:

```
                                    (SEQ ID NO: 4)
H-Aib-QGTFTSDYSKYLDΨRAAKDFIEWLESA;
                                    (SEQ ID NO: 5)
H-Aib-QGTFTSDYSKYLDΨRAAKDFIEWLESA;
                                    (SEQ ID NO: 6)
H-Aib-QGTFTSDYSKYLEΨRAAKDFIEWLESA;
                                    (SEQ ID NO: 7)
H-Ac4c-QGTFTSDYSKYLDΨRAAKDFIEWLESA;
and
                                    (SEQ ID NO: 8)
H-Aib-QGTFTSDYSKYLEΨRAAHDFIEWLESA,
```

-continued e.g. from (SEQ ID NO: 35)
H-Aib-QGTFTSDYSKYLD-K([17-carboxy-heptadecanoyl]-
isoGlu-Peg3-Peg3)-RAAKDFIEWLESA;

(SEQ ID NO: 36)
H-Aib-QGTFTSDYSKYLD-K([17-carboxy-heptadecanoyl]-
isoGlu-GSGSGG)-RAAKDFIEWLESA;

(SEQ ID NO: 37)
H-Aib-QGTFTSDYSKYLE-K([17-carboxy-heptadecanoyl]-
isoGlu-GSGSGG)-RAAKDFIEWLESA;

(SEQ ID NO: 38)
H-Ac4c-QGTFTSDYSKYLD-K([17-carboxy-heptadecanoyl]-
isoGlu-GSGSGG)-RAAKDFIEWLESA;
and (SEQ ID NO: 39)
H-Aib-QGTFTSDYSKYLE-K([17-carboxy-heptadecanoyl]-
isoGlu-Peg3-Peg3)-RAAHDFIEWLESA.

The compound of the invention may be selected from:

(SEQ ID NO: 9)
H-H-Aib-QGTFTSDYSKYLDΨRAAKDFIEWLESA-NH$_2$;

(SEQ ID NO: 10)
H-H-Aib-QGTFTSDYSKYLDΨRAAKDFIEWLESA-NH$_2$;

(SEQ ID NO: 11)
H-H-Aib-QGTFTSDYSKYLEΨRAAKDFIEWLESA-NH$_2$;

(SEQ ID NO: 12)
H-H-Ac4c-QGTFTSDYSKYLDΨRAAKDFIEWLESA-NH$_2$;
and (SEQ ID NO: 13)
H-H-Aib-QGTFTSDYSKYLEΨRAAHDFIEWLESA-NH$_2$, e.g. from (SEQ ID NO: 40)
H-H-Aib-QGTFTSDYSKYLD-K([17-carboxy-
heptadecanoyl]-isoGlu-Peg3-Peg3)-RAAKDFIEWLESA-
NH$_2$;

(SEQ ID NO: 41)
H-H-Aib-QGTFTSDYSKYLD-K([17-carboxy-
heptadecanoyl]-isoGlu-GSGSGG)-RAAKDFIEWLESA-NH$_2$;

(SEQ ID NO: 42)
H-H-Aib-QGTFTSDYSKYLE-K([17-carboxy-
heptadecanoyl]-isoGlu-GSGSGG)-RAAKDFIEWLESA-NH$_2$;

(SEQ ID NO: 43)
H-H-Ac4c-QGTFTSDYSKYLD-K([17-carboxy-
heptadecanoyl]-isoGlu-GSGSGG)-RAAKDFIEWLESA-NH$_2$;
and (SEQ ID NO: 44)
H-H-Aib-QGTFTSDYSKYLE-K([17-carboxy-
heptadecanoyl]-isoGlu-Peg3-Peg3)-RAAHDFIEWLESA-
NH$_2$.

In alternative embodiments of the second aspect:
X2 is selected from Aib and Ac4c;
X3 is selected from Gln and His;
X15 is Asp;
X16 is Glu;
X17 is selected from Arg and ψ;
X18 is selected from Ala and Arg;
X20 is Lys;
X24 is selected from Glu and ψ;
X28 is selected from Ser and ψ;

In some embodiments, when X28 is ψ, X2 is Ac4c.

In some embodiments, when X3 is His, X2 is Ac4c and X17 is ψ.

In some embodiments, when X17 is ψ, $Z^2Z^1$ is [17-carboxy-heptadecanoyl]-isoGlu-Peg3-Peg3 or [17-carboxy-heptadecanoyl]-isoGlu.

In some embodiments, when X24 or X28 is ψ, $Z^2Z^1$ is [17-carboxy-heptadecanoyl]-isoGlu-GSGSGG (SEQ ID NO: 34).

$P^1$ may have a sequence selected from:

(SEQ ID NO: 14)
H-Aib-QGTFTSDYSKYLDEΨAAKDFIEWLESA;

(SEQ ID NO: 15)
H-Ac4c-QGTFTSDYSKYLDEΨRAKDFIEWLESA;

(SEQ ID NO: 16)
H-Ac4c-HGTFTSDYSKYLDEΨRAKDFIEWLESA;

(SEQ ID NO: 17)
H-Ac4c-QGTFTSDYSKYLDEΨAAKDFIEWLESA;

(SEQ ID NO: 18)
H-Ac4c-QGTFTSDYSKYLDEΨRAKDFIEWLESA;

(SEQ ID NO: 19)
H-Aib-QGTFTSDYSKYLDERAAKDFIΨWLESA;

(SEQ ID NO: 20)
H-Ac4c-QGTFTSDYSKYLDERAAKDFIΨWLESA;

(SEQ ID NO: 21)
H-Ac4c-QGTFTSDYSKYLDERRAKDFIΨWLESA;

(SEQ ID NO: 22)
H-Ac4c-QGTFTSDYSKYLDERAAKDFIEWLEΨA
and (SEQ ID NO: 23)
H-Ac4c-QGTFTSDYSKYLDERRAKDFIEWLEΨA, e.g. from (SEQ ID NO: 45)
H-Aib-QGTFTSDYSKYLDE-K([17-carboxy-heptadecanoyl]-
isoGlu)-AAKDFIEWLESA;

(SEQ ID NO: 46)
H-Ac4c-QGTFTSDYSKYLDE-K([17-carboxy-
heptadecanoyl]-isoGlu-Peg3-Peg3)-RAKDFIEWLESA;

(SEQ ID NO: 47)
H-Ac4c-HGTFTSDYSKYLDE-K([17-carboxy-
heptadecanoyl]-isoGlu-Peg3-Peg3)-RAKDFIEWLESA;

(SEQ ID NO: 48)
H-Ac4c-QGTFTSDYSKYLDE-K([17-carboxy-
heptadecanoyl]-isoGlu)-AAKDFIEWLESA;

(SEQ ID NO: 49)
H-Ac4c-QGTFTSDYSKYLDE-K([17-carboxy-
heptadecanoyl]-isoGlu)-RAKDFIEWLESA;

-continued (SEQ ID NO: 50)
H-Aib-QGTFTSDYSKYLDERAAKDFI-K([17-carboxy-heptadecanoyl]-isoGlu-GSGSGG)-WLESA;

(SEQ ID NO: 51)
H-Ac4c-QGTFTSDYSKYLDERAAKDFI-K([17-carboxy-heptadecanoyl]-isoGlu-GSGSGG)-WLESA;

(SEQ ID NO: 52)
H-Ac4c-QGTFTSDYSKYLDERRAKDFI-K([17-carboxy-heptadecanoyl]-isoGlu-GSGSGG)-WLESA;

(SEQ ID NO: 53)
H-Ac4c-QGTFTSDYSKYLDERAAKDFIEWLE-K([17-carboxy-heptadecanoyl]-isoGlu-GSGSGG)-A;
and (SEQ ID NO: 54)
H-Ac4c-QGTFTSDYSKYLDERRAKDFIEWLE-K([17-carboxy-heptadecanoyl]-isoGlu-GSGSGG)-A.

The compound of the invention may be selected from:

(SEQ ID NO: 24)
H-H-Aib-QGTFTSDYSKYLDEΨAAKDFIEWLESA-NH$_2$;

(SEQ ID NO: 25)
H-H-Ac4c-QGTFTSDYSKYLDEΨRAKDFIEWLESA-NH$_2$;

(SEQ ID NO: 26)
H-H-Ac4c-HGTFTSDYSKYLDEΨRAKDFIEWLESA-NH$_2$;

(SEQ ID NO: 27)
H-H-Ac4c-QGTFTSDYSKYLDEΨAAKDFIEWLESA-NH$_2$;

(SEQ ID NO: 28)
H-H-Ac4c-QGTFTSDYSKYLDEΨRAKDFIEWLESA-NH$_2$;

(SEQ ID NO: 29)
H-H-Aib-QGTFTSDYSKYLDERAAKDFIΨWLESA-NH$_2$;

(SEQ ID NO: 30)
H-H-Ac4c-QGTFTSDYSKYLDERAAKDFIΨWLESA-NH$_2$;

(SEQ ID NO: 31)
H-H-Ac4c-QGTFTSDYSKYLDERRAKDFIΨWLESA-NH$_2$;

(SEQ ID NO: 32)
H-H-Ac4c-QGTFTSDYSKYLDERAAKDFIEWLEΨA-NH$_2$;
and (SEQ ID NO: 33)
H-H-Ac4c-QGTFTSDYSKYLDERRAKDFIEWLEΨA-NH$_2$,
e.g. from (SEQ ID NO: 55)
H-H-Aib-QGTFTSDYSKYLDE-K([17-carboxy-heptadecanoyl]-isoGlu)-AAKDFIEWLESA-NH$_2$;

(SEQ ID NO: 56)
H-H-Ac4c-QGTFTSDYSKYLDE-K([17-carboxy-heptadecanoyl]-isoGlu-Peg3-Peg3)-RAKDFIEWLESA-NH$_2$;

(SEQ ID NO: 57)
H-H-Ac4c-HGTFTSDYSKYLDE-K([17-carboxy-heptadecanoyl]-isoGlu-Peg3-Peg3)-RAKDFIEWLESA-NH$_2$;

(SEQ ID NO: 58)
H-H-Ac4c-QGTFTSDYSKYLDE-K([17-carboxy-heptadecanoyl]-isoGlu)-AAKDFIEWLESA-NH$_2$;

(SEQ ID NO: 59)
H-H-Ac4c-QGTFTSDYSKYLDE-K([17-carboxy-heptadecanoyl]-isoGlu)-RAKDFIEWLESA-NH$_2$;

(SEQ ID NO: 60)
H-H-Aib-QGTFTSDYSKYLDERAAKDFI-K([17-carboxy-heptadecanoyl]-isoGlu-GSGSGG)-WLESA-NH$_2$;

(SEQ ID NO: 61)
H-H-Ac4c-QGTFTSDYSKYLDERAAKDFI-K([17-carboxy-heptadecanoyl]-isoGlu-GSGSGG)-WLESA-NH$_2$;

(SEQ ID NO: 62)
H-H-Ac4c-QGTFTSDYSKYLDERRAKDFI-K([17-carboxy-heptadecanoyl]-isoGlu-GSGSGG)-WLESA-NH$_2$;

(SEQ ID NO: 63)
H-H-Ac4c-QGTFTSDYSKYLDERAAKDFIEWLE-K([17-carboxy-heptadecanoyl]-isoGlu-GSGSGG)-A-NH$_2$;
and (SEQ ID NO: 64)
H-H-Ac4c-QGTFTSDYSKYLDERRAKDFIEWLE-K([17-carboxy-heptadecanoyl]-isoGlu-GSGSGG)-A-NH$_2$.

For the avoidance of doubt, in all aspects of the invention, those positions which are not expressly stated to permit variability are fixed and thus may only include the stated residue.

In all aspects, the compound of the invention comprises a residue ψ, i.e. a residue selected from Lys, Arg, Orn and Cys in which the side chain is conjugated to a substituent —$Z^2$—$Z^1$— as described in more detail below.

The substituent is conjugated to the functional group at the distal end of the side chain from the alpha-carbon. The normal ability of the Lys, Arg, Orn or Cys side chain to participate in interactions mediated by that functional group (e.g. intra- and inter-molecular interactions) may therefore be reduced or completely eliminated by the presence of the substituent. Thus, the overall properties of the compound may be relatively insensitive to changes in the actual amino acid present as residue ψ. Consequently, it is believed that any of the residues Lys, Arg, Orn and Cys may be present at any position where ψ is permitted. However, in certain embodiments, it may be advantageous that the amino acid component of ψ is Lys.

In some embodiments, —$Z^1$ is an acyl group of formula:

A-B-Alk-(CO)— or a sulfonyl group of formula:

A-B-Alk-(SO$_2$)—;

A is —COOH or a carboxylic acid bioisostere;
B is a bond, C$_6$arylene, or C$_6$arylene-O—;
Alk is a saturated or unsaturated fatty chain of 6 to 18 carbon atoms in length, optionally substituted with one or more substituents selected from fluoro, C$_{1-4}$alkyl, trifluoromethyl, hydroxymethyl, amino, hydroxyl, C$_{1-4}$alkoxy, oxo, and carboxyl;
—$Z^2$— is —$S_A$—, —$S_A$—$S_B$—, or —$S_B$—$S_A$—;
—$S_A$— is a single amino acid residue selected from γ-Glu, α-Glu, α-Asp, β-Asp, Ala, β-Ala β-aminopropanoic acid), and Gaba (4-aminobutanoic acid);

—$S_B$— is a linker of general formula:

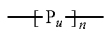

wherein n is 1-10 and each $P_U$ is independently selected from $P_U^i$ and $P_U^{iii}$;
each $P_U^i$ is independently a natural or unnatural amino acid residue; and
each $P_U^{iii}$ is independently a residue of general formula:

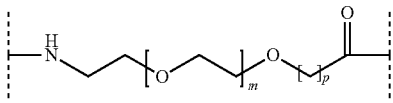

wherein m is 0-5 and p is 1, 3, 4, or 5.

In any aspect of the invention, $R^1$ may be selected from H and $C_{1-4}$ alkyl (e.g. methyl).

The compounds of the invention are glucagon analogue peptides. References herein to a glucagon analogue peptide should be construed as references to a compound of the invention or to a peptide $P^1$ or $P^1$—$P^2$ as the context requires. Reference to a compound of the invention should be taken to include any pharmaceutically acceptable salt (e.g. an acetate or chloride salt) or solvate thereof, unless otherwise stated or excluded by context.

The invention provides a composition comprising a compound of the invention as defined herein (including pharmaceutically acceptable salts or solvates thereof, as already described) in admixture with a carrier. In preferred embodiments, the composition is a pharmaceutical composition and the carrier is a pharmaceutically acceptable carrier. The glucagon analogue peptide may be in the form of a pharmaceutically acceptable salt of the glucagon analogue.

The compounds described herein find use, inter alia, in preventing weight gain or promoting weight loss. By "preventing" is meant inhibiting or reducing when compared to the absence of treatment, and is not necessarily meant to imply complete cessation of weight gain. The peptides may cause a decrease in food intake and/or increased energy expenditure, resulting in the observed effect on body weight. Independently of their effect on body weight, the compounds of the invention may have a beneficial effect on glucose control and/or on circulating cholesterol levels, being capable of lowering circulating LDL levels and increasing HDL/LDL ratio. Thus the compounds of the invention can be used for direct or indirect therapy of any condition caused or characterised by excess body weight, such as the treatment and/or prevention of obesity, morbid obesity, obesity linked inflammation, obesity linked gallbladder disease, obesity induced sleep apnea. They may also be used for the prevention of conditions caused or characterised by inadequate glucose control or dyslipidaemia (e.g. elevated LDL levels or reduced HDL/LDL ratio), diabetes (especially Type 2 diabetes), metabolic syndrome, hypertension, atherogenic dyslipidemia, atherosclerosis, arteriosclerosis, coronary heart disease, peripheral artery disease, stroke or microvascular disease. Their effects in these conditions may be as a result of or associated with their effect on body weight, or may be independent thereof.

The invention also provides a compound of the invention for use in a method of medical treatment, particularly for use in a method of treatment of a condition as described above.

The invention also provides the use of a compound of the invention in the preparation of a medicament for the treatment of a condition as described above.

The compound of the invention may be administered as part of a combination therapy with an agent for treatment of diabetes, obesity, dyslipidaemia or hypertension.

In such cases, the two active agents may be given together or separately, and as part of the same pharmaceutical formulation or as separate formulations.

Thus the compound of the invention can be used in combination with an anti-diabetic agent including but not limited to a biguanide (e.g. metformin), a sulfonylurea, a meglitinide or glinide (e.g. nateglinide), a DPP-IV inhibitor, an SGLT2 inhibitor, a glitazone, an insulin, or an insulin analogue. Examples of insulin analogues include but are not limited to Lantus™, Novorapid™, Humalog™, Novomix™, Actraphane HM™, Levemir™ and Apidra™.

The compound can further be used in combination with an anti-obesity agent including but not limited to a glucagon-like peptide receptor 1 agonist, peptide YY or analogue thereof, cannabinoid receptor 1 antagonist, lipase inhibitor, melanocortin receptor 4 agonist, melanin concentrating hormone receptor 1 antagonist, phentermine (alone or in combination with topiramate), a combination of norepinephrine/dopamine reuptake inhibitor and opioid receptor antagonist (e.g. a combination of bupropion and naltrexone), or a serotonergic agent (e.g. lorcaserin).

The compound can further be used in combination with an anti-hypertension agent including but not limited to an angiotensin-converting enzyme inhibitor, angiotensin II receptor blocker, diuretic, beta-blocker, or calcium channel blocker.

The compound can be used in combination with an anti-dyslipidaemia agent including but not limited to a statin, a fibrate, a niacin or a cholesterol absorbtion inhibitor.

Thus the invention further provides a composition or therapeutic kit comprising a compound of the invention and for example an anti-diabetic agent, anti-obesity agent, anti-hypertension agent or anti-dyslipidaemia agent as described above. Also provided is such a composition or therapeutic kit for use in a method of medical treatment, especially for treament of a condition as described above.

The compound of the invention may be made by synthetic chemistry. Accordingly the invention provides a method of synthesis of a compound of the invention.

The invention may also be made by a combination of recombinant and synthetic methods. The method may comprise expressing a precursor peptide sequence, optionally purifying the compund thus produced, and adding or modifying one or more amino acids to produce a compound of the invention or a compound comprising the amino acid sequence $P^1$ or $P^1$—$P^2$. The step of modification may comprise introduction of an Orn residue (e.g. by modification of a precursor residue) and/or introduction of a substituent Z2Z1 at the site of a residue ψ.

The precursor peptide may be expressed from a nucleic acid encoding the precursor peptide in a cell or a cell-free expression system comprising such a nucleic acid.

DETAILED DESCRIPTION OF THE INVENTION

Throughout this specification, the conventional one letter and three letter codes for naturally occurring amino acids are used, as well as generally accepted abbreviations for other amino acids, such as Aib (α-aminoisobutyric acid), Orn (ornithine), Dbu (2,4-diaminobutyric acid), Dpr (2,3-diaminopropanoic acid), Ac3c (1-amino-cyclopropanecarboxylic acid), Ac4c (1-amino-cyclobutanecarboxylic acid) and Ac5c (1-amino-cyclopentanecarboxylic acid).

Ac3c, Ac4c and Ac5c have similar structures and are to some extent interchangeable, although Ac4c may be preferred.

Glucagon is a 29-amino acid peptide that corresponds to amino acids 53 to 81 of pre-proglucagon and has the sequence His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr. Oxyntomodulin (OXM) is a 37 amino acid peptide which includes the complete 29 amino acid sequence of glucagon with an octapeptide carboxyterminal extension (amino acids 82 to 89 of pre-proglucagon, having the sequence Lys-Arg-Asn-Arg-Asn-Asn-Ile-Ala and termed "intervening peptide 1" or IP-1; the full sequence of human oxyntomodulin is thus His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala). The major biologically active fragment of GLP-1 is produced as a 30-amino acid, C-terminally amidated peptide that corresponds to amino acids 98 to 127 of pre-proglucagon.

The term "native glucagon" thus refers to native human glucagon having the sequence H-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-G n-Trp-Leu-Met-Asn-Thr-OH.

Amino acids within the sequence $P^1$ of the compounds of the invention can be considered to be numbered consecutively from 1 to 29 in the conventional N-terminal to C-terminal direction. Reference to a "position" within $P^1$ should be construed accordingly, as should reference to positions within native human glucagon and other molecules.

A compound of the invention may comprise a C-terminal peptide sequence $P^2$ of 1-20 amino acids, for example to stabilise the conformation and/or secondary structure of the glucagon analogue peptide, and/or to render the glucagon analogue peptide more resistant to enzymatic hydrolysis, e.g. as described in WO99/46283.

When present, $P^2$ represents a peptide sequence of 1-20 amino acid residues, e.g. in the range of 1-15, more preferably in the range of 1-10, in particular in the range of 1-7 amino acid residues, e.g., 1, 2, 3, 4, 5, 6 or 7 amino acid residues, such as 6 amino acid residues. Each of the amino acid residues in the peptide sequence $P^2$ may independently be selected from Ala, Leu, Ser, Thr, Tyr, Cys, Glu, Lys, Arg, Dbu (2,4-diaminobutyric acid), Dpr (2,3-diaminopropanoic acid) and Orn (ornithine). Preferably, the amino acid residues are selected from Ser, Thr, Tyr, Glu, Lys, Arg, Dbu, Dpr and Orn, more preferably selected exclusively from Glu, Lys, and Cys. The above-mentioned amino acids may have either D- or L-configuration, which in certain embodiments, have an L-configuration. Particularly preferred sequences $P^2$ are sequences of four, five, six or seven consecutive lysine residues (i.e. $Lys_3$, $Lys_4$, $Lys_5$, $Lys_6$ or $Lys_7$), and particularly five or six consecutive lysine residues. Other exemplary sequences of $P^2$ are shown in WO 01/04156. Alternatively the C-terminal residue of the sequence $P^2$ may be a Cys residue. This may assist in modification (e.g. PEGylation, or conjugation to albumin) of the compound. In such embodiments, the sequence $P^2$ may, for example, be only one amino acid in length (i.e. $P^2$=Cys) or may be two, three, four, five, six or even more amino acids in length. The other amino acids therefore serve as a spacer between the peptide $P^1$ and the terminal Cys residue.

The peptide sequence $P^2$ has no more than 25% sequence identity with the corresponding sequence of the IP-1 portion of human OXM (which has the sequence Lys-Arg-Asn-Arg-Asn-Asn-Ile-Ala).

"Percent (%) amino acid sequence identity" of a given peptide or polypeptide sequence with respect to another polypeptide sequence (e.g. IP-1) is calculated as the percentage of amino acid residues in the given peptide sequence that are identical with correspondingly positioned amino acid residues in the corresponding sequence of that other polypeptide when the two are aligned with one another, introducing gaps for optimal alignment if necessary. % identity values may be determined using WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Thus, when $P^2$ is aligned optimally with the 8 amino acids of IP-1, it has no more than two amino acids which are identical with the corresponding amino acids of IP-1.

In certain embodiments, $P^2$ is absent.

ψ is a residue of Lys, Arg, Orn or Cys whose side chain is conjugated to a substituent $Z^2$—$Z^1$.

Without wishing to be bound by any particular theory, it is thought that the substituent binds plasma proteins (e.g. albumin) in the blood stream, thus shielding the compounds of the invention from enzymatic degradation and thereby enhancing the half-life of the compounds. It may also modulate the potency of the compound, e.g. with respect to the glucagon receptor and/or the GLP-1 receptor.

The group $Z^1$ $Z^1$ is a fatty chain having a connection to $Z^2$, referred to herein as —X— and, at the end of the chain distal from the connection to $Z^2$, a polar group. —X— may be, for example, a bond, acyl (—CO—), sulfinyl (—SO—), or sulfonyl (—SO$_2$—), the connection being located at the ω-position with respect to the polar group, that is, at the end of the chain distal from the polar group.

Preferably, the polar group is an acidic or weakly acid group, for example a carboxylic acid or a carboxylic acid bioisostere, a phosphonate, or a sulfonate. The polar group may have a p$K_a$ of between −2 and 12 in water, more preferably between 1 and 7, more preferably between 3 and 6. Certain preferred polar groups have a p$K_a$ of between 4 and 5.

The polar group preferably comprises a carboxylic acid or carboxylic acid bioisostere. Suitable carboxylic acid bioisosteres are known in the art. Preferably the bioisostere has a proton having a p$K_a$ similar to the corresponding carboxylic acid. Examples of suitable bioisoteres may include, not by way of limitation, tetrazole, acylsulfomides, acylhydroxylamine, and squaric acid derivatives, as shown below (--- indicates the point of attachment):

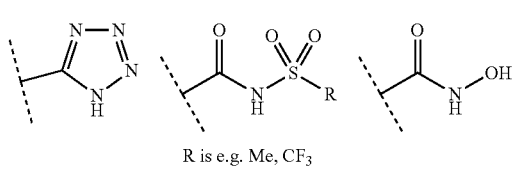

R is e.g. Me, CF$_3$

-continued

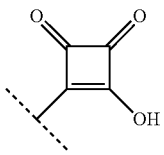

The polar group may be a group of formula A-B—, wherein A is a carboxylic acid (—COOH) or a carboxylic acid bioisostere, a phosphonic acid (—P(O)(OH)$_2$), or a sulfonic acid (—SO$_2$OH) group, and B is a bond or linker between A and the fatty chain. In some embodiments, the polar group is —COOH, that is, A is —COOH and B is a bond.

When B is a linker, it may be a cycloalkylene, heterocycloalkylene, C$_6$arylene, or C$_{5-6}$heteroarylene, or C$_6$arylene-O— or C$_{5-6}$heteroarylene-O—.

When B is phenylene it may, for example, be selected from 1,2-phenylene, 1,3-phenylene, 1,4-phenylene, preferably 1,4-phenylene (so that A-B— is a 4-benzoic acid substituent or 4-benzoic acid bioisostere). When B is phenylene-O—, it may, for example, be selected from 1,2-phenylene-O—, 1,3-phenylene-O—, 1,4-phenylene-O—, preferably 1,4-phenylene-O. Each phenylene of B may be optionally substituted with one or more substituents selected from fluoro, methyl, trifluoromethyl, amino, hydroxyl, and C$_{1-4}$alkoxy, preferably methoxy. It will be appreciated that substituent identity and position may be selected to subtly alter the pK$_a$ of the polar group. Suitable inductively or mesomerically electron-withdrawing or donating groups and their positional effects are known in the art. In some embodiments, B may be C$_{5-6}$heteroarylene, for example, pyridinylene or thiofuranylene, and may be optionally substituted as described.

For example, in some embodiments, A-B— may be selected from:

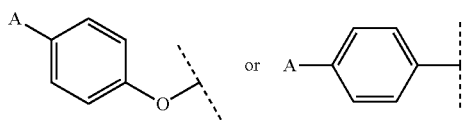

Preferably, A is —COOH. In some preferred polar groups, A is a carboxylic acid and B is C$_6$arylene-O—.

Fatty chain as used herein refers to a moiety comprising a chain of carbon atoms, the carbon atoms being predominantly substituted with hydrogen or hydrogen-like atoms, for example, a hy-drocarbon chain. Such fatty chains are often referred to as lipophilic, although it will be appreciated that substitution may alter the lipophilic properties of the overall molecule.

The fatty chain may by aliphatic. It may be entirely saturated or may include one or more double or triple bonds. Each double bond, if present, may be in the E or Z configuration. The fatty chain may also have one or more cycloalkylene or heterocycloalkylene moieties in its length, and additionally or alternatively may have one or more arylene or heteroarylene moieties in its length. For example, the fatty chain may incorporate a phenylene or piperazinylene moiety in its length as, for example, shown below (wherein --- represents the points of attachment within the chain).

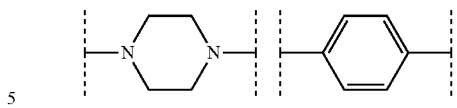

The fatty chain may be derived from a fatty acid, for example, it may be derived from a medium-chain fatty acid (MCFA) with an aliphatic tail of 6-12 carbon atoms, a long-chain fatty acid (LCFA) with an aliphatic tail of 13-21 carbon atoms, or a very long-chain fatty acid (LCFA) with an aliphatic tail of 22 carbon atoms or more. Examples of linear saturated fatty acids from which suitable fatty chains may be derived include tridecylic (tridecanoic) acid, myristic (tetradecanoic) acid, pentadecylic (pentadecanoic) acid, palmitic (hexadecanoic) acid, and margaric (heptadecanoic) acid. Examples of linear unsaturated fatty acids from which suitable fatty chains may be derived include myristoleic acid, palmitoleic acid, sapienic acid and oleic acid.

The fatty chain may be connected to Z$^2$ by an amide linkage, a sulfinamide linkage, a sulfonamide linkage, or by an ester linkage, or by an ether, thioether or amine linkage. Accordingly, the fatty chain may have at the ω position, that is, the position distal to the polar group, a bond to Z$^2$ or an acyl (—CO—), sulfinyl (—SO—), or sulfonyl (—SO$_2$—) group. Preferably, the fatty chain has an acyl (—CO—) group at the position distal to the polar group and is connected to Z$^2$ by an amide or ester linkage.

In some embodiments, Z$^1$ is a group of formula:

A-B-Alk-X— where A-B— is the polar group defined above, X is a bond, acyl (—CO—), sulfinyl (—SO—), or sulfonyl (—SO$_2$—), and Alk is a fatty chain that may be optionally substituted with one or more substituents. The fatty chain is preferably 6 to 18 carbon atoms in length (e.g. a C$_{6-18}$alkylene), more preferably, 8 to 18 carbons in length (e.g. a C$_{8-18}$alkylene), more preferably, 12 to 16 carbons in length (e.g. C$_{12-16}$alkylene), and may be saturated or unsaturated. Preferably, Alk is saturated, that is, preferably Alk is alkylene.

In some embodiments, Z$^1$ is an acyl group of formula:

A-B-Alk-(CO)— or a sulfonyl group of formula:

A-B-Alk-(SO$_2$)—.

Optional substituents on the fatty chain may be independently selected from fluoro, C$_{1-4}$alkyl, preferably methyl; trifluoromethyl, hydroxymethyl, amino, hydroxyl, C$_{1-4}$alkoxy, preferably methoxy; oxo, and carboxyl, and may be independently located at any point along the chain. In some embodiments, each optional substituent is selected from fluoro, methyl, and hydroxyl. Where more than one substituent is present, substituents may be the same or different. Preferably, the number of substituents is 0 to 3; more preferably the fatty chain is unsubstituted.

Preferably, Z$^1$ is an acyl group of formula:

A-B-alkylene-(CO)—

Where A and B are as defined above.

In some embodiments, Z$^1$ is:
4-carboxyphenoxynonanoyl HOOC—C$_6$H$_4$—O—(CH$_2$)$_8$—(CO)—.

Certain preferred Z$^1$ are derived from long-chain saturated α,ω-dicarboxylic acids of formula HOOC—(CH$_2$)$_{12-18}$—COOH, preferably, long-chain saturated α,ω- dicarboxylic acids having an even number of carbon atoms in the aliphatic chain. For example, and not by way of limitation, $Z^1$ may be:
13-carboxytridecanoyl HOOC—$(CH_2)_{12}$—(CO)—
15-carboxpentadecanoyl HOOC—$(CH_2)_{14}$—(CO)—; or
17-carboxyheptadecanoyl HOOC—$(CH_2)_{16}$—(CO)—.

The carboxylic acid group may be replaced by a bioisotere as detailed herein.

The Group $Z^2$ $Z^2$ is spacer that connects $Z^1$ to the side chain of the amino acid component of ψ. At its most general, $Z^2$ is a spacer bound at one terminus by Y, which may be a nitrogen, oxygen or sulfur atom, and at the other terminus by X, which may be a bond or an acyl (—CO—), sulfinyl (—SO—), or sulfonyl (—$SO_2$—). Accordingly, $Z^2$ may be a spacer of formula (--- indicate points of attachment):

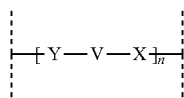

wherein:

Y may be —NH, —NR, —S or —O, where R may be alkyl, a protecting group or may form a linkage to another part of the spacer, with the remaining valency forming a linkage to Z;

X may be a bond, CO—, SO—, or $SO_2$—, with the remaining valency forming a linkage to the side chain of the amino acid component of ψ;

V is a bivalent organic moiety linking Y and X;

and n may be 1, 2, 3, 4, 5, 6, 7, 8, 9 or 10. Where n is 2 or more, each Y, V, and X is independent of every other Y, V, and X.

Accordingly, $Z^2$ may be bound at each side by amide, sulfinamide, sulfonamide, or ester linkages or by amino, ether, or thioether linkages depending upon the nature of Y and X and the corresponding linking groups on $Z^1$ and the side chain. Preferably, when Y is —S, X is a bond. Where n is 2 or greater, each V may also be bound to each adjacent V by linkages as described. Preferably, linkages are amides, esters or sulfonamides, most preferably amides. Accordingly, in some embodiments, each Y is —NH or —NR and each X is CO— or $SO_2$—.

In some embodiments, $Z^2$ is a spacer of formula —$S_A$—, —$S_B$—, —$S_A$—$S_B$— or —$S_B$—$S_A$—, wherein $S_A$ and $S_B$ are as defined below.

In some embodiments, $Z^2$ is selected from —$S_A$— or —$S_B$—$S_A$—, that is, [side chain]-$Z^2Z^1$ is [side chain]-$S_A$—$Z^1$ or [side chain]-$S_B$—$S_A$—$Z^1$.

The Group $S_A$ $S_A$ may be a single amino acid residue or a residue of an amino acid derivative, especially an amino acid derivative residue having a sulfinyl or sulfonyl in place of the carboxy moiety at the C terminus. Additionally or alternatively, the single amino acid residue may have an oxygen or sulfur atom in place of the nitrogen atom at the N terminus. Preferably, $S_A$ is a single amino acid residue.

In some embodiments, the amino acid may be selected from γ-Glu, α-Glu, α-Asp, 3-Asp, Ala, 3-Ala β-aminopropanoic acid), and Gaba (4-aminobutanoic acid). It will be understood that amino acids may be D or L, or a racemic or enantioenriched mixture. In some embodiments, the amino acid is an L-amino acid. In some embodiments, the amino acid is a D-amino acid.

In some preferred embodiments, $S_A$ has a carboxylic acid substituent, with γ-Glu, α-Glu, α-Asp, and β-Asp, and sulfinyl and sulfonyl derivatives thereof, being preferred. Accordingly, in some embodiments, the amino acid residue is:

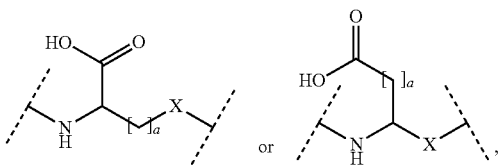

where —X— is —CO—, —SO—, —$SO_2$—, preferably —CO—, and a is 1 or 2, preferably 2. In some embodiments, the carboxylic acid is an ester, and the amino acid residue is:

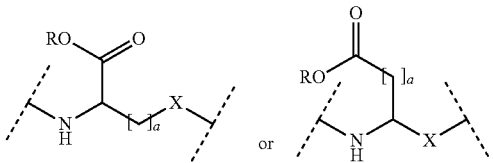

where —X— is —CO—, —SO—, —$SO_2$—, preferably —CO—, and a is 1 or 2, preferably 2, and R is $C_{1-4}$alkyl or $C_6$aryl. Preferably R is $C_{1-4}$alkyl, preferably methyl or ethyl, more preferably ethyl.

Preferably, $S_A$ is γ-Glu.

The Group $S_B$ $S_B$ may be a linker of general formula:

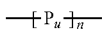

wherein $P_U$ is a polymeric unit and n is 1, 2, 3, 4, 5, 6, 7, 8, 9 or 10. One terminus of the linker $S_B$ is an —NH, —NR, —S or —O, wherein R may be alkyl, a protecting group or may form a linkage to another part of the polymeric unit; while the other is a bond or CO—, SO— or $SO_2$—. Accordingly, each polymeric unit $P_U$ may be bound at each side by amide, sulfinamide, sulfonamide, or ester linkages or by amino, ether, or thioether linkages depending upon the nature of Y and X and the corresponding linking groups on $Z^1$, $S_A$, and Lys.

In some embodiments, each $P_U$ may be independently a unit of formula:

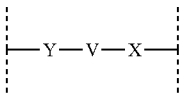

wherein:

Y may be —NH, —NR, —S or —O, wherein R may be alkyl, a protecting group or may form a linkage to another part of the spacer, with the remaining valency forming a linkage to $Z^1$;

X may be a bond, CO—, SO—, or $SO_2$—, with the remaining valency forming a linkage to Lys;

and V is a bivalent organic moiety linking Y and X.

In some embodiments, V is the α-carbon of a natural or unnatural amino acid, that is V is —CHR$^{AA}$—, wherein R$^{AA}$ is an amino acid side chain; or V is an optionally substituted C$_{1-6}$alkylene, or V is a chain comprising one or more units of ethylene glycol in series, also known as PEG chain, for example, —CH$_2$CH$_2$(OCH$_2$CH$_2$)$_m$—O—(CH$_2$)$_p$—, where m is 0, 1, 2, 3, 4, or 5, and p is 1, 2, 3, 4, or 5; when X is CO—, p is preferably 1, 3, 4, or 5. Optional alkylene substituents include fluoro, methyl, hydroxy, hydroxymethy, and amino.

Preferred P$_U$ units include:

(i). Single amino acid residues: P$_U^i$;

(ii). Dipeptide residues: P$_U^{ii}$; and (iii). Amino-(PEG)$_m$-carboxylic acid residues: P$_U^{iii}$, and may be present in any combination or order. For example, S$_B$ may comprise one or more of each of P$_U^i$, P$_U^{ii}$, and P$_U^{iii}$ in any order, or may comprise one or more units of P$_U^i$, P$_U^{ii}$, and P$_U^{iii}$ only, or one of more units selected from P$_U^i$ and P$_U^{ii}$, P$_U^i$ and P$_U^{iii}$, or P$_U^{ii}$ and P$_U^{iii}$.

(i). P$_U^i$ single amino acid residues

Each P$_U^i$ may be independently selected from any natural or unnatural amino acid residue and, for example, may be selected from Gly, Pro, Ala, Val, Leu, Ile, Met, Cys, Phe, Tyr, Trp, His, Lys, Arg, Gin, Asn, α-Glu, γ-Glu, Asp, Ser Thr, Gaba, Aib, 13-Ala, 5-aminopentanoyl, 6-aminohexanoyl, 7-aminoheptanoyl, 8-aminooctanoyl, 9-aminononanoyl, and 10-aminodecanoyl. Preferably, P$_U^i$ amino acid residues are selected from Gly, Ser, Ala, Thr, and Cys, more preferably from Gly and Ser.

In some embodiments, S$_B$ is —(P$_U^i$)$_n$—, wherein n is 1 to 8, more preferably 5 to 7, most preferably 6. In some preferred embodiments, S$_B$ is —(P$_U^i$)$_n$—, n is 6 and each P$_U^i$ is independently selected from Gly or Ser, with a preferred sequence being -Gly-Ser-Gly-Ser-Gly-Gly-.

(ii). P$_U^{ii}$ dipeptide residues

Each P$_U^{ii}$ may be independently selected from any dipeptide residue comprising two natural or unnatural amino acid residues bound by an amide linkage. Preferred P$_U^{ii}$ dipeptide residues include Gly-Gly, Gly-Ser, Ser-Gly, Gly-Ala, Ala-Gly, and Ala-Ala, more preferably Gly-Ser and Gly-Gly.

In some embodiments, S$_B$ is —(P$_U^{ii}$)$_n$—, wherein n is 2 to 4, more preferably 3, and each P$_U^{ii}$ is independently selected from Gly-Ser and Gly-Gly. In some preferred embodiments S$_B$ is —(P$_U^{ii}$)$_n$—, n is 3 and each P$_U^{ii}$ is independently selected from Gly-Ser and Gly-Gly, with a preferred sequence being -(Gly-Ser)-(Gly-Ser)-(Gly-Gly).

Amino acids having stereogenic centres within P$_U^i$ and P$_U^{ii}$ may be racemic, enantioenriched, or enantiopure. In some embodiments, the or each amino acid is independently an L-amino acid. In some embodiments, the or each amino acid is independently a D-amino acid.

(iii). P$_U^{iii}$ amino-(PEG)$_m$-carboxylic acid residues

Each P$_U^{iii}$ may be independently a residue of general formula:

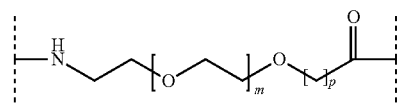

wherein m is 0, 1, 2, 3, 4, or 5, preferably 1 or 2, and p is 1, 3, 4, or 5, preferably 1.

In some embodiments, m is 1 and p is 1, that is, P$_U^{iii}$ is a residue of 8-amino-3,6-dioxaoctanoic acid (also known as {2-[2-aminoethoxy]ethoxy}acetic acid and H$_2$N-PEG$_3$-COOH). This residue is referred to herein as -PEG$_3$-.

In some embodiments, m is 2 and p is 1, that is, P$_U^{iii}$ is a residue of 11-amino-3,6,9-trioxaundecanoic acid (also known as H$_2$N-PEG$_4$-COOH). This residue is referred to herein as -PEG$_4$-.

In some embodiments, S$_B$ is —(P$_U^{iii}$)$_n$—, wherein n is 1 to 3, more preferably 2.

In some preferred embodiments, S$_B$ is selected from -PEG$_3$-PEG$_3$- and -PEG$_4$-PEG$_4$-.

Preferred —Z$^2$—Z$^1$

It will be understood that the above preferences may be independently combined to give preferred —Z$^2$—Z$^1$ combinations.

Some preferred —Z$^2$—Z$^1$ combinations are shown below (in each case, --- indicates the point of attachment to the side chain of the amino acid component of ψ:

(i)

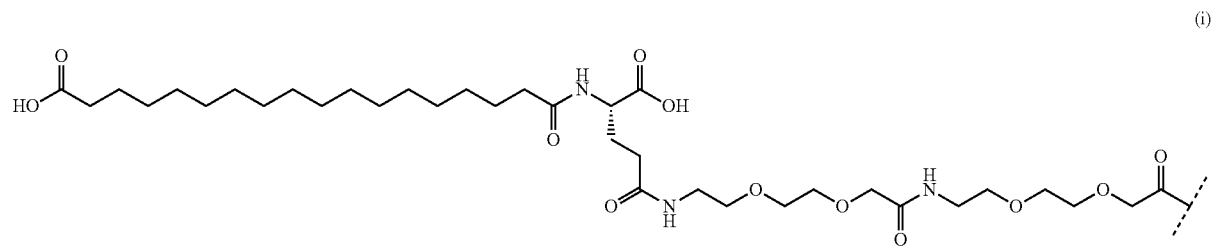

[17-Carboxy-heptadecanoyl]-isoGlu-Peg3-Peg3

(ii)

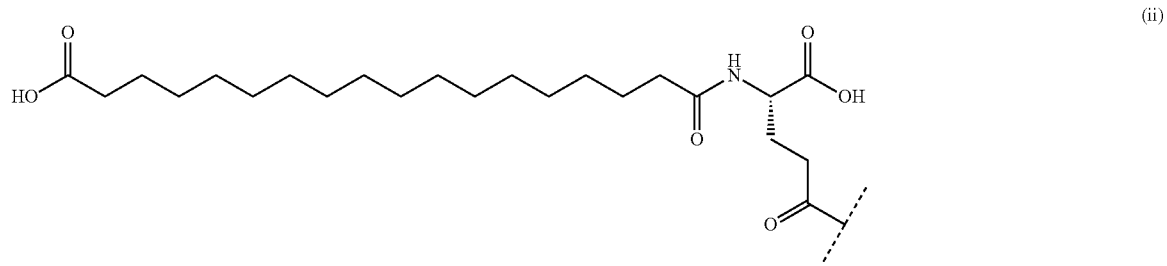

[17-Carboxy-heptadecanoyl]-isoGlu (iii)
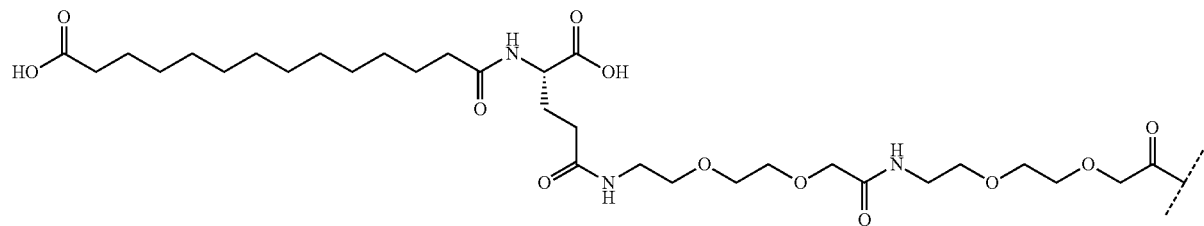
[13-Carboxy-tridecanoyl]-isoGlu-Peg3-Peg3
(iv)
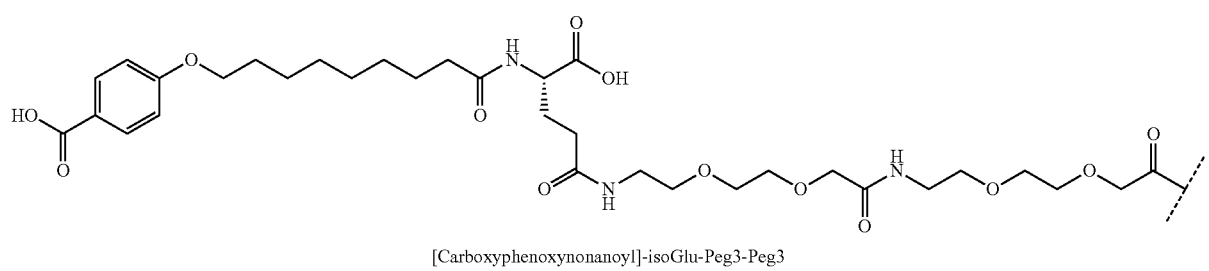
[Carboxyphenoxynonanoyl]-isoGlu-Peg3-Peg3
(v)
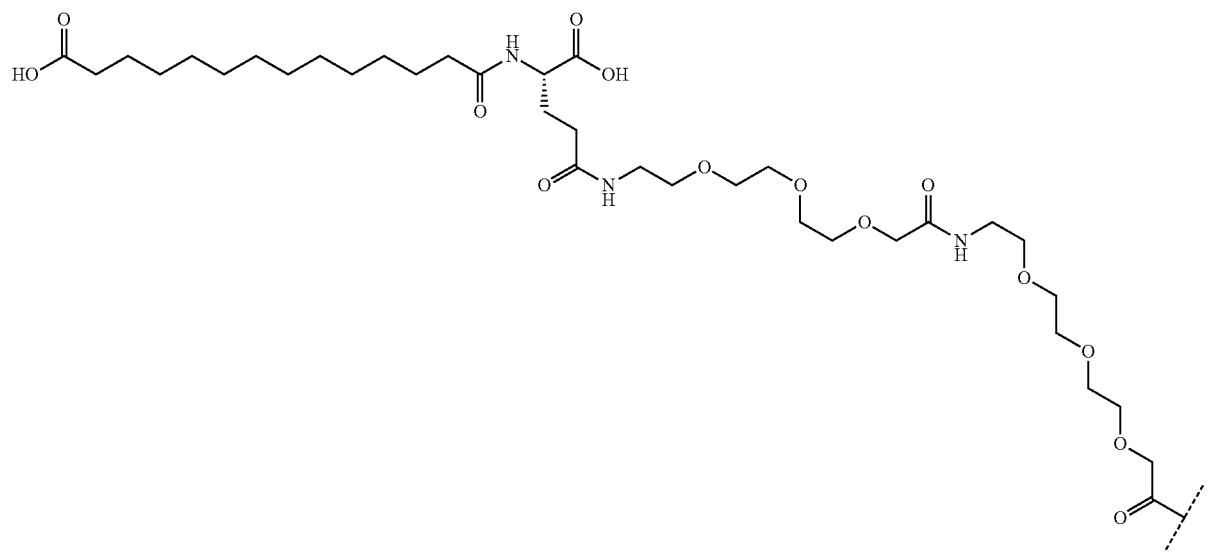
[13-Carboxy-tridecanoyl]-isoGlu-Peg4-Peg4
(vi)
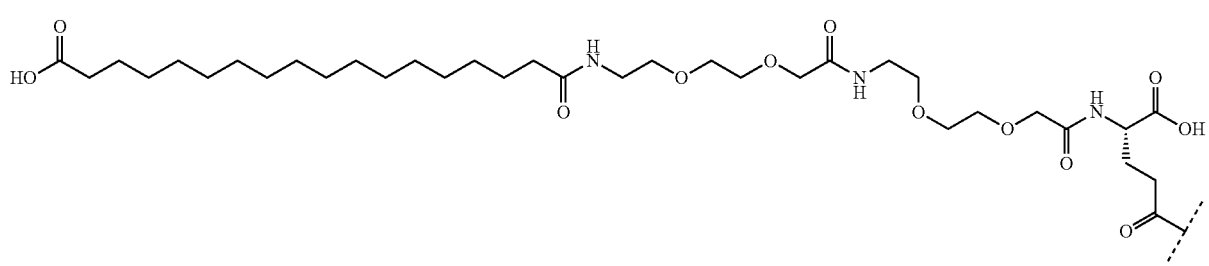
[17-Carboxy-heptadecanoyl]-Peg3-Peg3-isoGlu

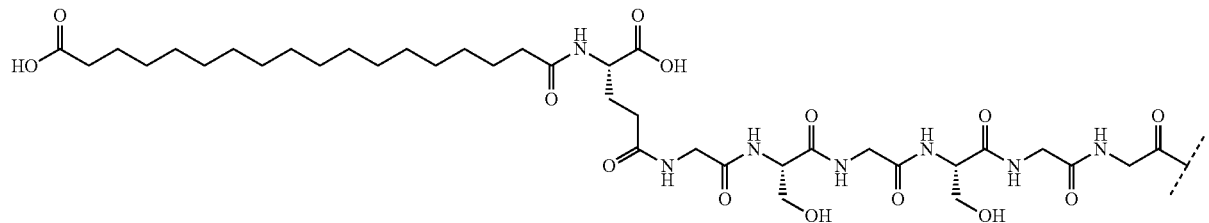

[17-Carboxy-heptadecanoyl]-isoGlu-GSGSGG (SEQ ID NO: 34)

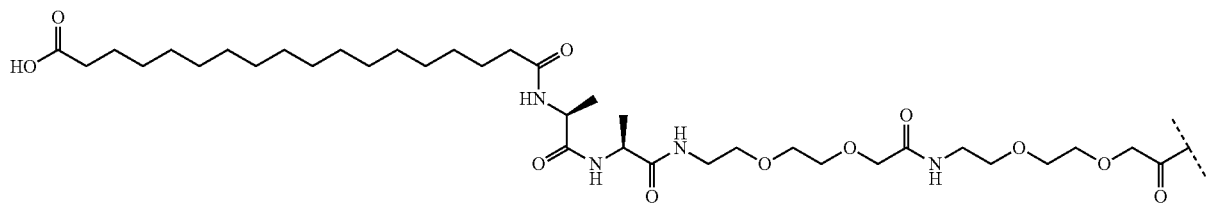

[17-Carboxy-heptadecanoyl]-AA-Peg3-Peg3

The presence of the polar group at the end of $Z^1$ is believed to enhance the pharmacokinetic properties of the compound, for example, by increasing half life and/or mean residence time, and reducing clearance. The linker may also contribute to these pharmacokinetic properties. Linkers comprising more than one amino acid unit (or moieties of similar size) may improve pharmacokinetic properties compared to those consisting of just one amino acid unit or the like. These properties may enable the compound to be administered less frequently than an equivalent compound with the same peptide backbone but no modification or a different modification (e.g. a substituent with an aliphatic fatty chain lacking a polar group and/or having a shorter linker moiety).

Without wishing to be bound by any particular theory, the inventors have found that, especially when longer linkers were included, the polar or charged group at the end of $Z^1$ may be capable of participating in an undesirable intramolecular nteraction with the free N-terminus of the molecule which might compromise the beneficial effects of the polar group on pharmacokinetics. The peptide backbones of the compounds described herein are belived to adopt relatively well-defined helical secondary structure, so the capacity of the polar group to engage in such interactions may depend on its location within the molecule. When located towards the C-terminus, interaction with the N-terminus may be relatively unlikely. However, the inventors were surprised to find that the substituent could be located at residues 16 and 17 of the molecule without necessarily compromising the pharmacokinetic benefits obtained.

The term "conjugated" is used here to describe the physical attachment of one identifiable chemical moiety to another, and the structural relationship between such moieties. It should not be taken to imply any particular method of synthesis.

The skilled reader will be well aware of suitable techniques that can be used to perform the coupling reactions using general synthetic methodologies listed e.g. in "Comprehensive Organic Transformations, A Guide to Functional Group Preparations", 2nd edition, Larock, R. C.; Wiley-VCH: New York, 1999. Such transformations may take place at any suitable stage during the synthesis process.

Peptide Synthesis

The compounds of the present invention may be manufactured either by standard synthetic methods, recombinant expression systems, or any other state of the art method. Thus the glucagon analogues may be synthesized in a number of ways, including, for example, a method which comprises:

(a) synthesizing the peptide by means of solid-phase or liquid-phase methodology, either stepwise or by fragment assembly, and isolation and purifying of the final peptide product; or (b) expressing a precursor peptide sequence from a nucleic acid construct that encodes the precursor peptide, recovering the expression product, and modifying the precursor peptide to yield a compound of the invention.

Expression is typically performed from a nucleic acid encoding the precursor peptide, which may be performed in a cell or a cell-free expression system comprising such a nucleic acid.

It is preferred to synthesize the analogues of the invention by means of solid-phase or liquid-phase peptide synthesis. In this context, reference is made to WO 98/11125 and, among many others, Fields, G B et al., 2002, "Principles and practice of solid-phase peptide synthesis". In: Synthetic Peptides (2nd Edition), and the Examples herein.

For recombinant expression, the nucleic acid fragments encoding the precursor peptide will normally be inserted in suitable vectors to form cloning or expression vectors. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) are capable of autonomous replication, thereby enabling high copy-numbers for the purposes of high-level expression or high-level replication for subsequent cloning.

In general outline, an expression vector comprises the following features in the 5'→3' direction and in operable linkage: a promoter for driving expression of the nucleic acid fragment, optionally a nucleic acid sequence encoding a leader peptide enabling secretion (to the extracellular phase or, where applicable, into the periplasma), the nucleic acid fragment encoding the precursor peptide, and optionally a nucleic acid sequence encoding a terminator. They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The vectors of the invention are used to transform host cells to produce the precursor peptide. Such transformed cells can be cultured cells or cell lines used for propagation of the nucleic acid fragments and vectors, and/or used for recombinant production of the precursor peptides.

Preferred transformed cells are micro-organisms such as bacteria [such as the species *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (e.g., *Saccharomyces cerevisiae* and *Pichia pastoris*), and protozoans. Alternatively, the transformed cells may be derived from a multicellular organism, i.e. it may be fungal cell, an insect cell, an algal cell, a plant cell, or an animal cell such as a mammalian cell. For the purposes of cloning and/or optimised expression it is preferred that the transformed cell is capable of replicating the nucleic acid fragment of the invention. Cells expressing the nucleic fragment can be used for small-scale or large-scale preparation of the peptides of the invention.

When producing the precursor peptide by means of transformed cells, it is convenient, although far from essential, that the expression product is secreted into the culture medium.

Efficacy

Binding of the relevant compounds to GLP-1 or glucagon (Glu) receptors may be used as an indication of agonist activity, but in general it is preferred to use a biological assay which measures intracellular signalling caused by binding of the compound to the relevant receptor. For example, activation of the glucagon receptor by a glucagon agonist will stimulate cellular cyclic AMP (cAMP) formation. Similarly, activation of the GLP-1 receptor by a GLP-1 agonist will stimulate cellular cAMP formation. Thus, production of cAMP in suitable cells expressing one of these two receptors can be used to monitor the relevant receptor activity. Use of a suitable pair of cell types, each expressing one receptor but not the other, can hence be used to determine agonist activity towards both types of receptor.

The skilled person will be aware of suitable assay formats, and examples are provided below. The GLP-1 receptor and/or the glucagon receptor may have the sequence of the receptors as described in the examples. For example, the assays may employ the human glucagon receptor (Glucagon-R) having primary accession number GI:4503947 and/or the human glucagon-like peptide 1 receptor (GLP-1R) having primary accession number GI:166795283. (in that where sequences of precursor proteins are referred to, it should of course be understood that assays may make use of the mature protein, lacking the signal sequence).

$EC_{50}$ values may be used as a numerical measure of agonist potency at a given receptor. An $EC_{50}$ value is a measure of the concentration of a compound required to achieve half of that compound's maximal activity in a particular assay. Thus, for example, a compound having $EC_{50}$[GLP-1] lower than the $EC_{50}$[GLP-1] of glucagon in a particular assay may be considered to have higher GLP-1 receptor agonist potency than glucagon.

The compounds described in this specification are typically GluGLP-1 dual agonists, as determined by the observation that they are capable of stimulating cAMP formation at both the glucagon receptor and the GLP-1 receptor. The stimulation of each receptor can be measured in independent assays and afterwards compared to each other.

By comparing the $EC_{50}$ value for the GLP-1 receptor ($EC_{50}$ [GLP-1-R]) with the $EC_{50}$ value for the Glucagon receptor, ($EC_{50}$ [GlucagonR]) for a given compound. the relative GLP-1R selectivity can be calculated as follows:

$$\text{Relative } GLP\text{-}1R\text{selectivity [compound]}=(EC_{50}[GLP\text{-}1R])/(EC_{50}[\text{Glucagon-}R])$$

The term "$EC_{50}$" stands for the half maximal Effective Concentration, typically at a particular receptor, or on the level of a particular marker for receptor function, and can refer to an inhibitory or an antagonistic activity, depending on the specific biochemical context.

Without wishing to be bound by any particular theory, a compound's relative selectivity may allow its effect on the GLP-1 or glucagon receptor to be compared directly to its effect on the other receptor. For example, the higher a compound's relative GLP-1 selectivity is, the more effective that compound may be on the GLP-1 receptor as compared to the glucagon receptor. Typically the results are compared for glucagon and GLP-1 receptors from the same species, e.g. human glucagon and GLP-1 receptors, or murine glucagon and GLP-1 receptors.

The compounds of the invention may have a higher relative GLP-1R selectivity than human glucagon in that for a particular level of glucagon-R agonist activity, the compound may display a higher level of GLP-1R agonist activity (i.e. greater potency at the GLP-1 receptor) than glucagon. It will be understood that the absolute potency of a particular compound at the glucagon and GLP-1 receptors may be higher, lower or approximately equal to that of native human glucagon, as long as the appropriate relative GLP-1R selectivity is achieved.

Nevertheless, the compounds of this invention may have a lower $EC_{50}$ [GLP-1R] than human glucagon. The compounds may have a lower $EC_{50}$[GLP-1-R] than glucagon while maintaining an $EC_{50}$ [Glucagon-R] that is less than 10-fold higher than that of human glucagon, less than 5-fold higher than that of human glucagon, or less than 2-fold higher than that of human glucagon.

The compounds of the invention may have an $EC_{50}$ [Glucagon-R] that is less than two-fold that of human glucagon. The compounds may have an $EC_{50}$ [Glucagon-R] that is less than two-fold that of human glucagon and have an $EC_{50}$ [GLP-1R] that is less than half that of human glucagon, less than a fifth of that of human glucagon, or less than a tenth of that of human glucagon.

The relative GLP-1R selectivity of the compounds may be between 0.05 and 20. For example, the compounds may have a relative selectivity of 0.05-0.20, 0.1-0.30, 0.2-0.5, 0.3-0.7, or 0.5-1.0; 1.0-2.0, 1.5-3.0, 2.0-4.0 or 2.5-5.0; or 0.05-20, 0.075-15, 0.1-10, 0.15-5, 0.75-2.5 or 0.9-1.1.

In certain embodiments, it may be desirable that $EC_{50}$ of any given compound for both the Glucagon-R and GLP-1R, e.g. for the human glucagon and GLP-1 receptors, should be less than 1 nM.

Therapeutic Uses

The compounds of the invention may provide attractive treatment and/or prevention options for, inter alia, obesity and metabolic diseases including diabetes, as discussed below.

Diabetes comprises a group of metabolic diseases characterized by hyperglycemia resulting from defects in insulin secretion, insulin action, or both. Acute signs of diabetes include excessive urine production, resulting compensatory thirst and increased fluid intake, blurred vision, unexplained weight loss, lethargy, and changes in energy metabolism. The chronic hyperglycemia of diabetes is associated with long-term damage, dysfunction, and failure of various organs, notably the eyes, kidneys, nerves, heart and blood vessels. Diabetes is classified into type 1 diabetes, type 2 diabetes and gestational diabetes on the basis on pathogenetic characteristics.

Type 1 diabetes accounts for 5-10% of all diabetes cases and is caused by auto-immune destruction of insulin-secreting pancreatic 3-cells.

Type 2 diabetes accounts for 90-95% of diabetes cases and is a result of a complex set of metabolic disorders. Type 2 diabetes is the consequence of endogenous insulin production becoming insufficient to maintain plasma glucose levels below the diagnostic thresholds.

Gestational diabetes refers to any degree of glucose intolerance identified during pregnancy.

Pre-diabetes includes impaired fasting glucose and impaired glucose tolerance and refers to those states that occur when blood glucose levels are elevated but below the levels that are established for the clinical diagnosis for diabetes.

A large proportion of people with type 2 diabetes and pre-diabetes are at increased risk of morbidity and mortality due to the high prevalence of additional metabolic risk factors including abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension) a prothrombotic state (e.g. high fibrinogen or plasminogen activator inhibitor-1 in the blood), and proinflammatory state (e.g., elevated C-reactive protein in the blood).

Conversely, obesity confers an increased risk of developing pre-diabetes, type 2 diabetes as well as e.g. certain types of cancer, obstructive sleep apnea and gall-blader disease.

Dyslipidaemia is associated with increased risk of cardiovascular diasese. High Density Lipoprotein (HDL) is of clinical importance since an inverse correlation exists between plasma HDL concentrations and risk of atherosclerotic disease. The majority of cholesterol stored in atherosclerotic plaques originates from LDL and hence elevated concentrations Low Density Lipoproteins (LDL) is closely associated with atherosclerosis. The HDL/LDL ratio is a clinical risk indictor for atherosclerosis and coronary atherosclerosis in particular.

Metabolic syndrome is characterized by a group of metabolic risk factors in one person. They include abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension), insulin resistance and glucose intolerance, prothrombotic state (e.g. high fibrinogen or plasminogen activator inhibitor-1 in the blood), and proinflammatory state (e.g., elevated C-reactive protein in the blood).

Individuals with the metabolic syndrome are at increased risk of coronary heart disease and other diseases related to other manifestations of arteriosclerosis (e.g., stroke and peripheral vascular disease). The dominant underlying risk factors for this syndrome appear to be abdominal obesity.

Without wishing to be bound by any particular theory, it is believed that the compounds of the invention act as dual agonists both on the human glucagon-receptor and the human GLP1-receptor, abbreviated here as dual GluGLP-1 agonists. The dual agonist may combine the effect of glucagon, e.g. on fat metabolism, with the effect of GLP-1, e.g. on blood glucose levels and food intake. They may therefore act to accelerate elimination of excessive adipose tissue, induce sustainable weight loss, and improve glycaemic control. Dual GluGLP-1 agonists may also act to reduce cardiovascular risk factors such as high cholesterol, high LDL-cholesterol or low HDL/LDL cholesterol ratios.

The compounds of the present invention can therefore be used in a subject in need thereof as pharmaceutical agents for preventing weight gain, promoting weight loss, reducing excess body weight or treating obesity (e.g. by control of appetite, feeding, food intake, calorie intake, and/or energy expenditure), including morbid obesity, as well as associated diseases and health conditions including but not limited to obesity linked inflammation, obesity linked gallbladder disease and obesity induced sleep apnea. The compounds of the invention may also be used for treatment of conditions caused by or associated with impaired glucose control, including metabolic syndrome, insulin resistance, glucose intolerance, pre-diabetes, increased fasting glucose, type 2 diabetes, hypertension, atherosclerois, arteriosclerosis, coronary heart disease, peripheral artery disease and stroke, in a subject in need thereof. Some of these conditions can be associated with obesity. However, the effects of the compounds of the invention on these conditions may be mediated in whole or in part via an effect on body weight, or may be independent thereof.

The synergistic effect of dual GluGLP-1 agonists may also result in reduction of cardiovascular risk factors such as high cholesterol and LDL, which may be entirely independent of their effect on body weight.

Thus the invention provides the use of a compound of the invention in the treatment of a condition as described above, in an individual in need thereof.

The invention also provides a compound of the invention for use in a method of medical treatment, particularly for use in a method of treatment of a condition as described above.

In a preferred aspect, the compounds described may be used in treating diabetes, esp. type 2 diabetes.

In a specific embodiment, the present invention comprises use of a compound for treating diabetes, esp. type 2 diabetes in an individual in need thereof.

In a not less preferred aspect, the compounds described may be used in preventing weight gain or promoting weight loss.

In a specific embodiment, the present invention comprises use of a compound for preventing weight gain or promoting weight loss in an individual in need thereof.

In a specific embodiment, the present invention comprises use of a compound in a method of treatment of a condition caused or characterised by excess body weight, e.g. the treatment and/or prevention of obesity, morbid obesity, morbid obesity prior to surgery, obesity linked inflammation, obesity linked gallbladder disease, obesity induced sleep apnea, prediabetes, diabetes, esp. type 2 diabetes, hypertension, atherogenic dyslipidimia, atherosclerois, arteriosclerosis, coronary heart disease, peripheral artery disease, stroke or microvascular disease in an individual in need thereof.

In another aspect, the compounds described may be used in a method of lowering circulating LDL levels, and/or increasing HDL/LDL ratio.

In a specific embodiment, the present invention comprises use of a compound in a method of lowering circulating LDL levels, and/or increasing HDL/LDL ratio in an individual in need thereof.

In another aspect, the compounds described may be used in a method of lowering circulating triglyceride levels.

Pharmaceutical Compositions

The compounds of the present invention may be formulated as pharmaceutical compositions prepared for storage or administration. Such a composition typically comprises a therapeutically effective amount of a compound of the invention, in the appropriate form, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials. The compounds of the present invention may be particularly useful for treatment of humans.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically acceptable salt" refers to a salt of any one of the compounds of the invention. Salts include pharmaceutically acceptable salts such as acid addition salts and basic salts. Examples of acid addition salts include hydrochloride salts, citrate salts and acetate salts.

Examples of basic salts include salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms (e.g. weight gain, hyperglycemia) when compared to the absence of treatment, and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. In certain embodiments, packaged forms include a label or insert with instructions for use. Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, and transdermal) administration. The formulations may conveniently be presented in unit dosage form and may be prepared by any of the methods well known in the art of pharmacy.

Subcutaneous or transdermal modes of administration may be particularly suitable for the compounds described herein.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Combination Therapy

A compound or composition of the invention may be administered as part of a combination therapy with an agent for treatment of obesity, hypertension, dyslipidemia or diabetes.

In such cases, the two active agents may be given together or separately, and as part of the same pharmaceutical formulation or as separate formulations.

Thus a compound or composition of the invention can further be used in combination with an anti-obesity agent, including but not limited to a glucagon-like peptide receptor 1 agonist, peptide YY or analogue thereof, cannabinoid receptor 1 antagonist, lipase inhibitor, melanocortin receptor 4 agonist, melanin concentrating hormone receptor 1 antagonist, phentermine (alone or in combination with topiramate), a combination of norepinephrine/dopamine reuptake inhibitor and opioid receptor antagonist (e.g. a combination of bupropion and naltrexone), or a serotonergic agent (e.g. lorcaserin).

A compound or composition of the invention can be used in combination with an anti-hypertension agent, including but not limited to an angiotensin-converting enzyme inhibitor, angiotensin II receptor blocker, diuretics, beta-blocker, or calcium channel blocker.

A compound or composition of the invention can be used in combination with a dyslipidaemia agent, including but not limited to a statin, a fibrate, a niacin and/or a cholesterol absorbtion inhibitor.

Further, a compound or composition of the invention can be used in combination with an anti-diabetic agent, including but not limited to a biguanide (e.g. metformin), a sulfonylurea, a meglitinide or glinide (e.g. nateglinide), a DPP-IV inhibitor, an SGLT2 inhibitor, a glitazone, a different GLP-1 agonist, an insulin or an insulin analogue. In a preferred embodiment, the compound or salt thereof is used in combination with insulin or an insulin analogue, DPP-IV inhibitor, sulfonylurea or metformin, particularly sulfonylurea or metformin, for achieving adequate glycemic control. Examples of insulin analogues include but are not limited to Lantus, Novorapid, Humalog, Novomix, and Actraphane HM, Levemir and Apidra.

EXAMPLES

Example 1: General Synthesis of Glucagon Analogues

Solid phase peptide synthesis (SPPS) was performed on a microwave assisted synthesizer using standard Fmoc strategy in NMP on a polystyrene resin (TentaGel S Ram). HATU was used as coupling reagent together with DIPEA as base. Piperidine (20% in NMP) was used for deprotection. Pseudoprolines: Fmoc-Phe-Thr(psiMe,Mepro)-OH and Fmoc-Asp-Ser(psiMe,Mepro)-OH (purchased from NovaBiochem) were used where applicable.

Abbreviations employed are as follows:
Boc: tert-butyloxycarbonyl
ivDde: 1-(4,4-dimethyl-2,6-dioxocyclohexylidene)3-methyl-butyl
Dde: 1-(4,4-dimethyl-2,6-dioxocyclohexylidene)-ethyl
DCM: dichloromethane
DMF: N,N-dimethylformamide
DIPEA: diisopropylethylamine
EDT: 1,2-ethanedithiol
EtOH: ethanol
Et20: diethyl ether
HATU: N-[(dimethylamino)-1H-1,2,3-triazol[4,5-b]pyridine-1-ylmethylene]-N-methylmethanaminium hexafluorophosphate N-oxide
MeCN: acetonitrile
NMP: N-methylpyrrolidone
TFA: trifluoroacetic acid
TIS: triisopropylsilane
Cleavage:

The crude peptide was cleaved from the resin by treatment with 95/2.5/2.5% (v/v) TFA/TIS/water at room temperature (r.t.) for 2 hours. Most of the TFA was removed at reduced pressure and the crude peptide was precipitated and washed with diethylether and allowed to dry to constant weight at ambient temperature.

The following compounds were synthesised:

```
                                                 (SEQ ID NO: 69)
1 H-H-Aib-QGTFTSDYSKYLDS-K([15-carboxypentadecanoyl]-isoGlu)-AAHDFVEWLLSA-

NH2

(SEQ ID NO: 40)
2 H-H-Aib-QGTFTSDYSKYLD-K([17-carboxyheptadecanoyl]-isoGlu-Peg3-Peg3)-

RAAKDFIEWLESA-NH2

(SEQ ID NO: 60)
3 H-H-Aib-QGTFTSDYSKYLDERAAKDFI-K([17-carboxyheptadecanoyl]-isoGlu-GSGSGG)-WLESA-NH2

(SEQ ID NO: 56)
4 H-H-Ac4c-QGTFTSDYSKYLDE-K([17-carboxyheptadecanoyl]-isoGlu-Peg3-Peg3)-RAKDFIEWLESA-NH2

(SEQ ID NO: 41)
5 H-H-Aib-QGTFTSDYSKYLD-K([17-carboxyheptadecanoyl]-isoGlu-GSGSGG)-RAAKDFIEWLESA-NH2

(SEQ ID NO: 42)
6 H-H-Aib-QGTFTSDYSKYLE-K([17-carboxyheptadecanoyl]-isoGlu-GSGSGG)-RAAKDFIEWLESA-NH2

(SEQ ID NO: 43)
7 H-H-Ac4c-QGTFTSDYSKYLD-K([17-carboxyheptadecanoyl]-isoGlu-GSGSGG)-RAAKDFIEWLESA-NH2

(SEQ ID NO: 44)
8 H-H-Aib-QGTFTSDYSKYLE-K([17-carboxyheptadecanoyl]-isoGlu-Peg3-Peg3)-RAAHDFIEWLESA-NH2

(SEQ ID NO: 57)
9 H-H-Ac4c-HGTFTSDYSKYLDE-K([17-carboxyheptadecanoyl]-isoGlu-Peg3-Peg3)-RAKDFIEWLESA-NH2

(SEQ ID NO: 55)
10 H-H-Aib-QGTFTSDYSKYLDE-K([17-carboxyheptadecanoyl]-isoGlu)-AAKDFIEWLESA-NH2
```

-continued

```
                                            (SEQ ID NO: 58)
11 H-H-Ac4c-QGTFTSDYSKYLDE-K([17-carboxyheptadecanoyl]-isoGlu)-AAKDFIEWLESA-NH2

(SEQ ID NO: 59)
12 H-H-Ac4c-QGTFTSDYSKYLDE-K([17-carboxyheptadecanoyl]-isoGlu)-RAKDFIEWLESA-NH2

(SEQ ID NO: 61)
13 H-H-Ac4c-QGTFTSDYSKYLDERAAKDFI-K([17-carboxyheptadecanoyl]-isoGlu-GSGSGG)-WLESA-NH2

(SEQ ID NO: 62)
14 H-H-Ac4c-QGTFTSDYSKYLDERRAKDFI-K([17-carboxyheptadecanoyl]-isoGlu-GSGSGG)-WLESA-NH2

(SEQ ID NO: 63)
15 H-H-Ac4c-QGTFTSDYSKYLDERAAKDFIEWLE-K([17- carboxy-heptadecanoyl]-isoGlu-GSGSGG)-A-NH2

(SEQ ID NO: 64)
16 H-H-Ac4c-QGTFTSDYSKYLDERRAKDFIEWLE-K([17- carboxy-heptadecanoyl]-isoGlu-GSGSGG)-A-NH2
```

The acylated GLP-1 analogue semaglutide was also synthesised, and has the structure:

```
                                            (SEQ ID NO: 70)
H-H-[2-methyl-Ala]-EGTFTSDVSSYLEGQAA- K([17-Carboxy-heptadecanoyl]-isoGlu- Peg3-Peg3)-EFIAWLVRGRG-OH.
```

Example 2: Glucagon Receptor and GLP-1-Receptor Efficacy Assays

The cDNA encoding either the human glucagon receptor (Glucagon-R) (primary accession number P47871) or the human glucagon-like peptide 1 receptor (GLP-1R) (primary accession number P43220) were synthesized and cloned into a mammalian expression vector containing a Zeocin resistance marker.

The mammalian expression vectors encoding the Glucagon-R or the GLP-1-R were transfected into Chinese hamster ovary (CHO) cells by the Attractene method method. Stably expressing clones were obtained by Zeocin selection (2501 µg/mL) upon limited dilution of cells resistant to the selection pressure. Glucagon-R and GLP-1-R cell clones expressing were picked, propagated and tested in the Glucagon-R and GLP-1-R efficacy assays as described below. One Glucagon-R expressing clone and one GLP-1-R expressing clone were chosen for compound profiling.

CHO cells expressing the human Glucagon-R, or human GLP-1-R were seeded 24 hours prior to the assay at 30,000 cells per well in 96-well microtiter plates in culture in 100 µl growth medium. On the day of analysis, growth medium was removed and the cells were washed once with 200 µl of assay buffer (Krebs-Ringer-buffer—KRBH). The buffer was removed and the cells were incubated for 15 min at room temperature in 10 µl KRBH (KRBH+10 mM HEPES, 5 mM NaHCO3, 0.1% (V/V) BSA) with 0.1 mM IBMX in deionized water containing increasing concentrations of test peptides. The reaction was stopped by the addition of lysis buffer (0.1% w/v BSA, 5 mM HEPES, 0.3% v/v Tween-20). After cell lysis for 10 min at room temperature, lysates were transferred to 384-well plates and 10 µl of acceptor/donor-bead mixture as contained in the AlphaScreen™ cAMP Functional Assay Kit was added. After one hour of incubation at room temperature in the dark, the cAMP content was determined applying the AlphaScreen™ cAMP Functional Assay Kit from Perkin-Elmer according to manufacturer instructions. $EC_{50}$ and relative efficacies compared to reference compounds (glucagon and GLP-1) were calculated applying computer aided curve fitting. The GLP-1/glucagon ratio is calculated as defined earlier. See Table 1.

TABLE 1

| Compound | EC50 hGCGR CHO-K1 [nM] | EC50 hGLP-1R CHO-K1 [nM] | Ratio GLP-1/ Glucagon |
|---|---|---|---|
| 1 | 0.21 nM | 0.38 nM | 1.81 |
| 2 | 0.13 nM | 1.76 nM | 13.54 |
| 3 | 1.48 nM | 0.70 nM | 0.47 |
| 4 | 0.45 nM | 0.70 nM | 1.56 |
| 5 | 0.18 nM | 0.83 nM | 4.61 |
| 6 | 0.44 nM | 1.43 nM | 3.25 |
| 7 | 0.11 nM | 0.97 nM | 8.82 |
| 8 | 0.31 nM | 0.80 nM | 2.58 |
| 9 | 0.07 nM | 0.97 nM | 13.86 |
| 10 | 1.08 nM | 0.41 nM | 0.38 |
| 11 | 0.28 nM | 0.56 nM | 2.00 |
| 12 | 0.07 nM | 0.48 nM | 6.86 |
| 13 | 0.52 nM | 0.33 nM | 0.63 |
| 14 | 0.18 nM | 0.60 nM | 3.33 |
| 15 | 0.92 nM | 0.61 nM | 0.65 |
| 16 | 0.16 nM | 0.53 nM | 3.31 |

Example 3: Agonistic Activity on Endogenous GLP-1 Receptor

Agonistic activity of the test compounds on endogenous GLP-1 receptors was determined using a murine insulinoma cell line. Intracellular cAMP was used an indicator of receptor activation.

Cells were cultured for 24 h at a density of 10,000 cells/well in a 384-well plate. Medium was removed and 10 µL KRBH buffer (NaCl 130 mM, KCl 3.6 mM, $NaH_2PO_4$ 0.5 mM, $MgSO_4$ 0.5 mM, $CaCl_2$ 1.5 mM) containing test compound or GLP-1 (at increasing concentrations from 0.1 µM to 100 nM) or solvent control (0.1% (v/v) DMSO) was added to the wells for 15 minutes at a temperature of 26° C.

The cellular cAMP content is measured using the AlphaScreen cAMP Functional Assay Kit (Perkin Elmer). Measurement was performed using the Envision (PerkinElmer) according to manufacturer's recommendations.

Results were converted into cAMP concentrations using a cAMP standard curve prepared in KRBH buffer containing 0.1% (v/v) DMSO. The resulting cAMP curves were plotted as absolute cAMP concentrations (nM) over log (test compound concentration) and analyzed using the curve fitting program XLfit.

Parameters calculated to describe both the potency as well as the agonistic activity of each test compound on the endogenous GLP-1 receptors were:

pEC50 (negative logarithmic value of EC50, a concentration resulting in a half-maximal elevation of cAMP levels, reflecting the potency of the test compound);

Percent control (% CTL)(% cAMP elevation for each test compound concentration normalized based on the GLP-1-induced maximum cAMP response (100% CTL)). See Table 2.

TABLE 2

| Compound | EC50 [nM] |
|---|---|
| 1 | 0.60 nM |
| 2 | 0.69 nM |
| 3 | 0.15 nM |
| 4 | 0.40 nM |
| 5 | 0.65 nM |
| 6 | 0.54 nM |
| 7 | 0.47 nM |
| 8 | 0.36 nM |
| 9 | 0.84 nM |
| 10 | 0.60 nM |
| 11 | 0.72 nM |
| 12 | 0.81 nM |
| 13 | 0.37 nM |
| 14 | 0.38 nM |
| 15 | 0.25 nM |
| 16 | 0.34 nM |

Example 4: Agonistic Activity on Endogenous Glucagon Receptor

Agonistic activity of the test compounds on endogenous glucagon receptor was determined by measuring their effect on rate of glycogen synthesis in primary rat hepatocytes. Upon activation of the glucagon receptor, an inhibition of the glycogen synthesis rate is expected. Rate of glycogen synthesis was determined by counting the amount of radioactively labeled glucose incorporated into the cellular glycogen stores in a defined period of time.

Primary rat hepatocytes were cultured at a density of 40,000 cells/well in a 24-well plate for 24 hours at 37° C. and 5% $CO_2$.

Medium was discarded and the cells washed with PBS. 180 μL of KRBH-based buffer containing 0.1% BSA and glucose at a concentration of 22.5 mM was then added to the wells, followed by test compound and 40 μCi/ml D-[U14C] glucose (20 μL each). Incubation was continued for 3 hours.

At the end of the incubation period, the incubation buffer was aspirated and cells washed once with ice-cold PBS before lysis by incubation for 30 min at room temperature with 100 μL 1 mol/l NaOH.

Cell lysates were transferred to 96-well filter plates and glycogen precipitated by incubating the filter-plates for 120 min at 4° C. followed by washing the filter plates 4 times with ice-cold ethanol (70%). The resulting precipitates were filtered to dryness and the amount of incorporated $^{14}C$-glucose determined by using a Topcount scintillation counter according to manufacturer's recommendations.

Wells with vehicle controls (0.1% (v/v) DMSO in KRBH buffer) were included as reference for non-inhibited glycogen synthesis (100% CTL). Wells without added D-[$U^{14}C$] glucose were included as controls for non-specific background signal (subtracted from all values). Endogenous glucagon peptide was used as a positive control.

All treatments were performed at least in duplicates.

Parameters calculated to describe both the potency as well as the agonistic activity of each test compound on the endogenous glucagon receptor are pEC50 and % CTL. % CTL is determined by calculating the percentage of CPM/well in the presence of the test compound compared to the CPM/well of the vehicle control after subtracting the background CPM/well:

[CPM/well(basal)−CPM/well(sample)]*100/[CPM/well(basal)−CPM/well(control)]

An activator of the glucagon receptor will result in an inhibition of the glycogen synthesis rate and will give % CTL values between 0% CTL (complete inhibition) and 100% CTL (no observable inhibition).

The resulting activity curves were plotted as absolute counts (unit: cpm/sample) over log (test compound concentration) and analyzed using the curve fitting program XLfit.

pEC50 (negative logarithmic value of EC50) reflects the potency of the test compound.

TABLE 3

| Compound | EC50 [nM] |
|---|---|
| 1 | 0.85 nM |
| 2 | 0.11 nM |
| 3 | 0.94 nM |
| 4 | 1.79 nM |
| 5 | 0.21 nM |
| 6 | 0.80 nM |
| 7 | 0.34 nM |
| 8 | 0.29 nM |
| 9 | 0.11 nM |
| 10 | 1.53 nM |
| 11 | 0.95 nM |
| 12 | 0.45 nM |
| 13 | 0.43 nM |
| 14 | 0.19 nM |
| 15 | 3.63 nM |
| 16 | 0.19 nM |

The terms $EC_{50}$ and $pEC_{50}$ quoted in relation to GLP-1R activation could equally be regarded as $IC_{50}$ and $pIC_{50}$ in relation to glycogen synthesis.

Example 5: Estimate of Pharmacokinetic Parameters

Pharmacokinetic parameters of the test compounds were determined after intravenous administration to Han/Wistar rats. The acylated GLP-1 analogue semaglutide was also tested for comparison purposes.

Male Wistar rats were obtained from Charles River (Germany) weighing approximately 180 to 210 g at time of arrival at the test facility. Rats were caged in European standard rat cages type IV with light cycle of 12-hour dark and 12-hour light. During the study rats were housed in standard rat cages type III. Both diet Altromin 1324 (Altromin, Germany) and water was administered ad libitum during the whole experimental period. The animals were housed in the test facility for at least 4 days in order to assure proper acclimatization.

The compounds were first dissolved in 0.1% aqueous ammonia to a nominal concentration of 2 mg/ml, and then diluted to the desired dosing strength (10 M) in sterile PBS containing 25 mM phosphate buffer, pH 7.4. Intravenous injections corresponding to 20 nmol/kg were given via a lateral tail vein.

Blood samples (200 μl) were collected from the periorbital plexus at time points 0.08, 0.25, 0.5, 1, 2, 4, 8, 24, 32 and 48 h post dosing into $K_3$EDTA tubes and centrifuged for 5 minutes at 4° C. within 20 minutes of sampling. Plasma samples (>100 μl) were transferred to 96-well PCR plates, immediately frozen and kept at −20° C. until analysed for plasma concentration for the respective GLP-1-glucagon compound using LC-MS/MS. Individual plasma concentration-time profiles were analysed by a non-compartmental approach using ToxKin™ version 3.2 (Unilog IT Services), and the resulting pharmacokinetic parameters were determined. See Table 4.

TABLE 4

| Compound | Clearance (ml/min/kg) | Terminal half life (h) | Mean Residence Time (h) |
|---|---|---|---|
| 2 | 0.11 | 9.1 | 13.6 |
| 3 | 0.056 | 23.4 | 28.7 |
| 4 | 0.11 | 13.7 | 17.6 |
| Semaglutide | 0.10 | 9.0 | 11.4 |

SEQUENCE LISTING

```
<160> NUMBER OF SEQ ID NOS: 70

<210> SEQ ID NO 1
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: SITE
<222> LOCATION: (1)..(1)
<223> OTHER INFORMATION: Linked to R1, wherein R1 is H, C1-4 alkyl,
      acetyl, formyl, benzoyl, trifluoroacetyl or pGlu
<220> FEATURE:
<221> NAME/KEY: VARIANT
<222> LOCATION: (2)..(2)
<223> OTHER INFORMATION: Xaa is selected from Aib (alpha-aminoisobutyric
      acid), Ac3c (1-amino-cyclopropanecarboxylic acid),
      Ac4c(1-amino-cyclobutanecarboxylic acid ) or Ac5c
      (1-amino-cyclopentanecarboxylic acid)
<220> FEATURE:
<221> NAME/KEY: VARIANT
<222> LOCATION: (3)..(3)
<223> OTHER INFORMATION: Xaa is selected from Gln or His
<220> FEATURE:
<221> NAME/KEY: VARIANT
<222> LOCATION: (15)..(15)
<223> OTHER INFORMATION: Xaa is selected from Asp or Glu
<220> FEATURE:
<221> NAME/KEY: VARIANT
<222> LOCATION: (16)..(16)
<223> OTHER INFORMATION: Xaa is selected from Glu or Psi, wherein Psi is
      a residue of Lys, Arg, Orn or Cys in which the side chain is
      conjugated to a substituent having the formula -Z2Z1, wherein Z1
      and Z2 are as defined in US 2015-0111826
<220> FEATURE:
<221> NAME/KEY: VARIANT
<222> LOCATION: (17)..(17)
<223> OTHER INFORMATION: Xaa is selected from Arg or Psi
<220> FEATURE:
<221> NAME/KEY: VARIANT
<222> LOCATION: (18)..(18)
<223> OTHER INFORMATION: Xaa is selected from Ala or Arg
<220> FEATURE:
<221> NAME/KEY: VARIANT
<222> LOCATION: (20)..(20)
<223> OTHER INFORMATION: Xaa is selected from Lys or His
<220> FEATURE:
<221> NAME/KEY: VARIANT
<222> LOCATION: (24)..(24)
<223> OTHER INFORMATION: Xaa is selected from Glu or Psi
<220> FEATURE:
<221> NAME/KEY: VARIANT
<222> LOCATION: (28)..(28)
<223> OTHER INFORMATION: Xaa is selected from Ser or Psi
<220> FEATURE:
<221> NAME/KEY: SITE
<222> LOCATION: (29)..(29)
<223> OTHER INFORMATION: Linked to P2-R2, wherein P2 is a sequence of
      1-20 amino acid units independently selected from the group
      consisting of Ala, Leu, Ser, Thr, Tyr, Cys, Glu, Lys, Arg, Dbu,
      Dpr and Orn, or is absent; and wherein R2 is OH or NH2

<400> SEQUENCE: 1

His Xaa Xaa Gly Thr Phe Thr Ser Asp Tyr Ser Lys Tyr Leu Xaa Xaa
```

```
1               5                   10                  15
Xaa Xaa Ala Xaa Asp Phe Ile Xaa Trp Leu Glu Xaa Ala
            20                  25

<210> SEQ ID NO 2
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is IsoGlu-

<400> SEQUENCE: 2

Xaa Gly Ser Gly Ser Gly Gly
1               5

<210> SEQ ID NO 3
<211> LENGTH: 2
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: -Peg3Peg3

<400> SEQUENCE: 3

Ala Ala
1

<210> SEQ ID NO 4
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (16)..(16)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 4

His Xaa Gln Gly Thr Phe Thr Ser Asp Tyr Ser Lys Tyr Leu Asp Xaa
1               5                   10                  15

Arg Ala Ala Lys Asp Phe Ile Glu Trp Leu Glu Ser Ala
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (15)..(15)
```

```
<223> OTHER INFORMATION: Xaa is Asp or Glu
<220> FEATURE:
<221> NAME/KEY: MISC_FEATURE
<222> LOCATION: (16)..(16)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 5

His Xaa Gln Gly Thr Phe Thr Ser Asp Tyr Ser Lys Tyr Leu Xaa Xaa
1               5                   10                  15

Arg Ala Ala Lys Asp Phe Ile Glu Trp Leu Glu Ser Ala
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (15)..(15)
<223> OTHER INFORMATION: Xaa is Asp or Glu
<220> FEATURE:
<221> NAME/KEY: MISC_FEATURE
<222> LOCATION: (16)..(16)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 6

His Xaa Gln Gly Thr Phe Thr Ser Asp Tyr Ser Lys Tyr Leu Xaa Xaa
1               5                   10                  15

Arg Ala Ala Lys Asp Phe Ile Glu Trp Leu Glu Ser Ala
            20                  25

<210> SEQ ID NO 7
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (2)..(2)
<223> OTHER INFORMATION: Ac4c
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (15)..(15)
<223> OTHER INFORMATION: Xaa is Asp or Glu
<220> FEATURE:
<221> NAME/KEY: misc_feature
<222> LOCATION: (16)..(16)
<223> OTHER INFORMATION: Xaa can be any naturally occurring amino acid

<400> SEQUENCE: 7

His Xaa Gln Gly Thr Phe Thr Ser Asp Tyr Ser Lys Tyr Leu Xaa Xaa
1               5                   10                  15

Arg Ala Ala Lys Asp Phe Ile Glu Trp Leu Glu Ser Ala
            20                  25
```

```
<210> SEQ ID NO 8
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (15)..(15)
<223> OTHER INFORMATION: Xaa is Asp or Glu
<220> FEATURE:
<221> NAME/KEY: MISC_FEATURE
<222> LOCATION: (16)..(16)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 8

His Xaa Gln Gly Thr Phe Thr Ser Asp Tyr Ser Lys Tyr Leu Xaa Xaa
1               5                   10                  15

Arg Ala Ala His Asp Phe Ile Glu Trp Leu Glu Ser Ala
            20                  25

<210> SEQ ID NO 9
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (16)..(16)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 9

His Xaa Gln Gly Thr Phe Thr Ser Asp Tyr Ser Lys Tyr Leu Asp Xaa
1               5                   10                  15

Arg Ala Ala Lys Asp Phe Ile Glu Trp Leu Glu Ser Ala
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
```

```
<221> NAME/KEY: MISC_FEATURE
<222> LOCATION: (16)..(16)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 10

His Xaa Gln Gly Thr Phe Thr Ser Asp Tyr Ser Lys Tyr Leu Asp Xaa
1               5                   10                  15

Arg Ala Ala Lys Asp Phe Ile Glu Trp Leu Glu Ser Ala
            20                  25

<210> SEQ ID NO 11
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (16)..(16)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 11

His Xaa Gln Gly Thr Phe Thr Ser Asp Tyr Ser Lys Tyr Leu Glu Xaa
1               5                   10                  15

Arg Ala Ala Lys Asp Phe Ile Glu Trp Leu Glu Ser Ala
            20                  25

<210> SEQ ID NO 12
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (16)..(16)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 12
```

His Xaa Gln Gly Thr Phe Thr Ser Asp Tyr Ser Lys Tyr Leu Asp Xaa
1               5                   10                  15

Arg Ala Ala Lys Asp Phe Ile Glu Trp Leu Glu Ser Ala
            20                  25

<210> SEQ ID NO 13
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (16)..(16)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 13

His Xaa Gln Gly Thr Phe Thr Ser Asp Tyr Ser Lys Tyr Leu Glu Xaa
1               5                   10                  15

Arg Ala Ala His Asp Phe Ile Glu Trp Leu Glu Ser Ala
            20                  25

<210> SEQ ID NO 14
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (17)..(17)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 14

His Xaa Gln Gly Thr Phe Thr Ser Asp Tyr Ser Lys Tyr Leu Asp Glu
1               5                   10                  15

Xaa Ala Ala Lys Asp Phe Ile Glu Trp Leu Glu Ser Ala
            20                  25

<210> SEQ ID NO 15
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:

```
<221> NAME/KEY: MISC_FEATURE
<222> LOCATION: (17)..(17)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 15

His Xaa Gln Gly Thr Phe Thr Ser Asp Tyr Ser Lys Tyr Leu Asp Glu
1               5                   10                  15

Xaa Arg Ala Lys Asp Phe Ile Glu Trp Leu Glu Ser Ala
            20                  25

<210> SEQ ID NO 16
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (17)..(17)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 16

His Xaa His Gly Thr Phe Thr Ser Asp Tyr Ser Lys Tyr Leu Asp Glu
1               5                   10                  15

Xaa Arg Ala Lys Asp Phe Ile Glu Trp Leu Glu Ser Ala
            20                  25

<210> SEQ ID NO 17
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (17)..(17)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 17

His Xaa Gln Gly Thr Phe Thr Ser Asp Tyr Ser Lys Tyr Leu Asp Glu
1               5                   10                  15

Xaa Ala Ala Lys Asp Phe Ile Glu Trp Leu Glu Ser Ala
            20                  25

<210> SEQ ID NO 18
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
```

```
<222> LOCATION: (17)..(17)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 18

His Xaa Gln Gly Thr Phe Thr Ser Asp Tyr Ser Lys Tyr Leu Asp Glu
1               5                   10                  15

Xaa Arg Ala Lys Asp Phe Ile Glu Trp Leu Glu Ser Ala
            20                  25

<210> SEQ ID NO 19
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (24)..(24)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 19

His Xaa Gln Gly Thr Phe Thr Ser Asp Tyr Ser Lys Tyr Leu Asp Glu
1               5                   10                  15

Arg Ala Ala Lys Asp Phe Ile Xaa Trp Leu Glu Ser Ala
            20                  25

<210> SEQ ID NO 20
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (24)..(24)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 20

His Xaa Gln Gly Thr Phe Thr Ser Asp Tyr Ser Lys Tyr Leu Asp Glu
1               5                   10                  15

Arg Ala Ala Lys Asp Phe Ile Xaa Trp Leu Glu Ser Ala
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (24)..(24)
```

-continued

```
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 21

His Xaa Gln Gly Thr Phe Thr Ser Asp Tyr Ser Lys Tyr Leu Asp Glu
1               5                   10                  15

Arg Arg Ala Lys Asp Phe Ile Xaa Trp Leu Glu Ser Ala
            20                  25

<210> SEQ ID NO 22
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (28)..(28)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 22

His Xaa Gln Gly Thr Phe Thr Ser Asp Tyr Ser Lys Tyr Leu Asp Glu
1               5                   10                  15

Arg Ala Ala Lys Asp Phe Ile Glu Trp Leu Glu Xaa Ala
            20                  25

<210> SEQ ID NO 23
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (28)..(28)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826

<400> SEQUENCE: 23

His Xaa Gln Gly Thr Phe Thr Ser Asp Tyr Ser Lys Tyr Leu Asp Glu
1               5                   10                  15

Arg Arg Ala Lys Asp Phe Ile Glu Trp Leu Glu Xaa Ala
            20                  25

<210> SEQ ID NO 24
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
```

-continued

```
<220> FEATURE:
<221> NAME/KEY: MISC_FEATURE
<222> LOCATION: (17)..(17)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 24

His Xaa Gln Gly Thr Phe Thr Ser Asp Tyr Ser Lys Tyr Leu Asp Glu
1               5                   10                  15

Xaa Ala Ala Lys Asp Phe Ile Glu Trp Leu Glu Ser Ala
            20                  25

<210> SEQ ID NO 25
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (17)..(17)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 25

His Xaa Gln Gly Thr Phe Thr Ser Asp Tyr Ser Lys Tyr Leu Asp Glu
1               5                   10                  15

Xaa Arg Ala Lys Asp Phe Ile Glu Trp Leu Glu Ser Ala
            20                  25

<210> SEQ ID NO 26
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (17)..(17)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2
```

<400> SEQUENCE: 26

His Xaa His Gly Thr Phe Thr Ser Asp Tyr Ser Lys Tyr Leu Asp Glu
1               5                   10                  15

Xaa Arg Ala Lys Asp Phe Ile Glu Trp Leu Glu Ser Ala
            20                  25

<210> SEQ ID NO 27
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (17)..(17)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 27

His Xaa Gln Gly Thr Phe Thr Ser Asp Tyr Ser Lys Tyr Leu Asp Glu
1               5                   10                  15

Xaa Ala Ala Lys Asp Phe Ile Glu Trp Leu Glu Ser Ala
            20                  25

<210> SEQ ID NO 28
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (17)..(17)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 28

His Xaa Gln Gly Thr Phe Thr Ser Asp Tyr Ser Lys Tyr Leu Asp Glu
1               5                   10                  15

Xaa Arg Ala Lys Asp Phe Ile Glu Trp Leu Glu Ser Ala
            20                  25

<210> SEQ ID NO 29
<211> LENGTH: 29

```
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (24)..(24)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 29

His Xaa Gln Gly Thr Phe Thr Ser Asp Tyr Ser Lys Tyr Leu Asp Glu
1               5                   10                  15

Arg Ala Ala Lys Asp Phe Ile Xaa Trp Leu Glu Ser Ala
            20                  25

<210> SEQ ID NO 30
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (24)..(24)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 30

His Xaa Gln Gly Thr Phe Thr Ser Asp Tyr Ser Lys Tyr Leu Asp Glu
1               5                   10                  15

Arg Ala Ala Lys Asp Phe Ile Xaa Trp Leu Glu Ser Ala
            20                  25

<210> SEQ ID NO 31
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
```

```
<223> OTHER INFORMATION: Xaa is Ac4c
<220> FEATURE:
<221> NAME/KEY: MISC_FEATURE
<222> LOCATION: (24)..(24)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 31

His Xaa Gln Gly Thr Phe Thr Ser Asp Tyr Ser Lys Tyr Leu Asp Glu
1               5                   10                  15

Arg Arg Ala Lys Asp Phe Ile Xaa Trp Leu Glu Ser Ala
            20                  25

<210> SEQ ID NO 32
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (28)..(28)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 32

His Xaa Gln Gly Thr Phe Thr Ser Asp Tyr Ser Lys Tyr Leu Asp Glu
1               5                   10                  15

Arg Ala Ala Lys Asp Phe Ile Glu Trp Leu Glu Xaa Ala
            20                  25

<210> SEQ ID NO 33
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MISC_FEATURE
<222> LOCATION: (28)..(28)
<223> OTHER INFORMATION: Xaa is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2
```

```
<400> SEQUENCE: 33

His Xaa Gln Gly Thr Phe Thr Ser Asp Tyr Ser Lys Tyr Leu Asp Glu
1               5                   10                  15

Arg Arg Ala Lys Asp Phe Ile Glu Trp Leu Glu Xaa Ala
            20                  25

<210> SEQ ID NO 34
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: Xaa is [17-carboxy-heptadecanoyl]-isoGlu-

<400> SEQUENCE: 34

Xaa Gly Ser Gly Ser Gly Gly
1               5

<210> SEQ ID NO 35
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (16)..(16)
<223> OTHER INFORMATION: K([17-carboxy-heptadecanoyl]-isoGlu-Peg3-Peg3)

<400> SEQUENCE: 35

His Xaa Gln Gly Thr Phe Thr Ser Asp Tyr Ser Lys Tyr Leu Asp Lys
1               5                   10                  15

Arg Ala Ala Lys Asp Phe Ile Glu Trp Leu Glu Ser Ala
            20                  25

<210> SEQ ID NO 36
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (16)..(16)
<223> OTHER INFORMATION: K([17-carboxy-heptadecanoyl]-isoGlu-GSGSGG)

<400> SEQUENCE: 36

His Xaa Gln Gly Thr Phe Thr Ser Asp Tyr Ser Lys Tyr Leu Asp Lys
1               5                   10                  15

Arg Ala Ala Lys Asp Phe Ile Glu Trp Leu Glu Ser Ala
            20                  25

<210> SEQ ID NO 37
<211> LENGTH: 29
<212> TYPE: PRT
<213> ORGANISM: Artificial Sequence
```

-continued

```
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (16)..(16)
<223> OTHER INFORMATION: ([17-carboxy-heptadecanoyl]-isoGlu-GSGSGG)

<400> SEQUENCE: 37

His Xaa Gln Gly Thr Phe Thr Ser Asp Tyr Ser Lys Tyr Leu Glu Lys
1               5                   10                  15

Arg Ala Ala Lys Asp Phe Ile Glu Trp Leu Glu Ser Ala
            20                  25

<210> SEQ ID NO 38
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (16)..(16)
<223> OTHER INFORMATION: ([17-carboxy-heptadecanoyl]-isoGlu-GSGSGG)

<400> SEQUENCE: 38

His Xaa Gln Gly Thr Phe Thr Ser Asp Tyr Ser Lys Tyr Leu Asp Lys
1               5                   10                  15

Arg Ala Ala Lys Asp Phe Ile Glu Trp Leu Glu Ser Ala
            20                  25

<210> SEQ ID NO 39
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (16)..(16)
<223> OTHER INFORMATION: ([17-carboxy-heptadecanoyl]-isoGlu-Peg3-Peg3)

<400> SEQUENCE: 39

His Xaa Gln Gly Thr Phe Thr Ser Asp Tyr Ser Lys Tyr Leu Glu Lys
1               5                   10                  15

Arg Ala Ala His Asp Phe Ile Glu Trp Leu Glu Ser Ala
            20                  25

<210> SEQ ID NO 40
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
```

```
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (16)..(16)
<223> OTHER INFORMATION: ([17-carboxy-heptadecanoyl]-isoGlu-Peg3-Peg3)
<220> FEATURE:
<221> NAME/KEY: MOD_RES
<222> LOCATION: (29)..(29)
<223> OTHER INFORMATION: NH2

<400> SEQUENCE: 40

His Xaa Gln Gly Thr Phe Thr Ser Asp Tyr Ser Lys Tyr Leu Asp Lys
1               5                   10                  15

Arg Ala Ala Lys Asp Phe Ile Glu Trp Leu Glu Ser Ala
            20                  25

<210> SEQ ID NO 41
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (16)..(16)
<223> OTHER INFORMATION: ([17-carboxy-heptadecanoyl]-isoGlu-GSGSGG)
<220> FEATURE:
<221> NAME/KEY: MOD_RES
<222> LOCATION: (29)..(29)
<223> OTHER INFORMATION: NH2

<400> SEQUENCE: 41

His Xaa Gln Gly Thr Phe Thr Ser Asp Tyr Ser Lys Tyr Leu Asp Lys
1               5                   10                  15

Arg Ala Ala Lys Asp Phe Ile Glu Trp Leu Glu Ser Ala
            20                  25

<210> SEQ ID NO 42
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (16)..(16)
<223> OTHER INFORMATION: ([17-carboxy-heptadecanoyl]-isoGlu-GSGSGG)
<220> FEATURE:
<221> NAME/KEY: MOD_RES
<222> LOCATION: (29)..(29)
<223> OTHER INFORMATION: NH2

<400> SEQUENCE: 42

His Xaa Gln Gly Thr Phe Thr Ser Asp Tyr Ser Lys Tyr Leu Glu Lys
```

Arg Ala Ala Lys Asp Phe Ile Glu Trp Leu Glu Ser Ala
            20                  25

<210> SEQ ID NO 43
<211> LENGTH: 29
<212> TYPE: PRT
<213> ORGANISM: Artificial Sequence
<220> FEATURE:
<223> OTHER INFORMATION: Synthetic consruct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (16)..(16)
<223> OTHER INFORMATION: ([17-carboxy-heptadecanoyl]-isoGlu-GSGSGG)
<220> FEATURE:
<221> NAME/KEY: MOD_RES
<222> LOCATION: (29)..(29)
<223> OTHER INFORMATION: NH2

<400> SEQUENCE: 43

His Xaa Gln Gly Thr Phe Thr Ser Asp Tyr Ser Lys Tyr Leu Asp Lys
1               5                   10                  15

Arg Ala Ala Lys Asp Phe Ile Glu Trp Leu Glu Ser Ala
            20                  25

<210> SEQ ID NO 44
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (16)..(16)
<223> OTHER INFORMATION: ([17-carboxy-heptadecanoyl]-isoGlu-Peg3-Peg3)
<220> FEATURE:
<221> NAME/KEY: MOD_RES
<222> LOCATION: (29)..(29)
<223> OTHER INFORMATION: NH2

<400> SEQUENCE: 44

His Xaa Gln Gly Thr Phe Thr Ser Asp Tyr Ser Lys Tyr Leu Glu Lys
1               5                   10                  15

Arg Ala Ala His Asp Phe Ile Glu Trp Leu Glu Ser Ala
            20                  25

<210> SEQ ID NO 45
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)

```
<223> OTHER INFORMATION: Xaa is Aib
<220> FEATURE:
<221> NAME/KEY: MOD_RES
<222> LOCATION: (17)..(17)
<223> OTHER INFORMATION: ([17-carboxy-heptadecanoyl]-isoGlu)

<400> SEQUENCE: 45

His Xaa Gln Gly Thr Phe Thr Ser Asp Tyr Ser Lys Tyr Leu Asp Glu
1               5                   10                  15

Lys Ala Ala Lys Asp Phe Ile Glu Trp Leu Glu Ser Ala
            20                  25

<210> SEQ ID NO 46
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (17)..(17)
<223> OTHER INFORMATION: ([17-carboxy-heptadecanoyl]-isoGlu-Peg3-Peg3)

<400> SEQUENCE: 46

His Xaa Gln Gly Thr Phe Thr Ser Asp Tyr Ser Lys Tyr Leu Asp Glu
1               5                   10                  15

Lys Arg Ala Lys Asp Phe Ile Glu Trp Leu Glu Ser Ala
            20                  25

<210> SEQ ID NO 47
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (17)..(17)
<223> OTHER INFORMATION: ([17-carboxy-heptadecanoyl]-isoGlu-Peg3-Peg3)

<400> SEQUENCE: 47

His Xaa His Gly Thr Phe Thr Ser Asp Tyr Ser Lys Tyr Leu Asp Glu
1               5                   10                  15

Lys Arg Ala Lys Asp Phe Ile Glu Trp Leu Glu Ser Ala
            20                  25

<210> SEQ ID NO 48
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (17)..(17)
<223> OTHER INFORMATION: ([17-carboxy-heptadecanoyl]-isoGlu)

<400> SEQUENCE: 48
```

His Xaa Gln Gly Thr Phe Thr Ser Asp Tyr Ser Lys Tyr Leu Asp Glu
1               5                   10                  15

Lys Ala Ala Lys Asp Phe Ile Glu Trp Leu Glu Ser Ala
            20                  25

<210> SEQ ID NO 49
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (17)..(17)
<223> OTHER INFORMATION: ([17-carboxy-heptadecanoyl]-isoGlu)

<400> SEQUENCE: 49

His Xaa Gln Gly Thr Phe Thr Ser Asp Tyr Ser Lys Tyr Leu Asp Glu
1               5                   10                  15

Lys Arg Ala Lys Asp Phe Ile Glu Trp Leu Glu Ser Ala
            20                  25

<210> SEQ ID NO 50
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (24)..(24)
<223> OTHER INFORMATION: ([17-carboxy-heptadecanoyl]-isoGlu-GSGSGG)

<400> SEQUENCE: 50

His Xaa Gln Gly Thr Phe Thr Ser Asp Tyr Ser Lys Tyr Leu Asp Glu
1               5                   10                  15

Arg Ala Ala Lys Asp Phe Ile Lys Trp Leu Glu Ser Ala
            20                  25

<210> SEQ ID NO 51
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (24)..(24)
<223> OTHER INFORMATION: ([17-carboxy-heptadecanoyl]-isoGlu-GSGSGG)

<400> SEQUENCE: 51

His Xaa Gln Gly Thr Phe Thr Ser Asp Tyr Ser Lys Tyr Leu Asp Glu
1               5                   10                  15

Arg Ala Ala Lys Asp Phe Ile Lys Trp Leu Glu Ser Ala
            20                  25

<210> SEQ ID NO 52
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (24)..(24)
<223> OTHER INFORMATION: ([17-carboxy-heptadecanoyl]-isoGlu-GSGSGG)

<400> SEQUENCE: 52

His Xaa Gln Gly Thr Phe Thr Ser Asp Tyr Ser Lys Tyr Leu Asp Glu
1               5                   10                  15

Arg Arg Ala Lys Asp Phe Ile Lys Trp Leu Glu Ser Ala
            20                  25

<210> SEQ ID NO 53
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (28)..(28)
<223> OTHER INFORMATION: ([17-carboxy-heptadecanoyl]-isoGlu-GSGSGG)

<400> SEQUENCE: 53

His Xaa Gln Gly Thr Phe Thr Ser Asp Tyr Ser Lys Tyr Leu Asp Glu
1               5                   10                  15

Arg Ala Ala Lys Asp Phe Ile Glu Trp Leu Glu Lys Ala
            20                  25

<210> SEQ ID NO 54
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (28)..(28)
<223> OTHER INFORMATION: ([17-carboxy-heptadecanoyl]-isoGlu-GSGSGG)

<400> SEQUENCE: 54

His Xaa Gln Gly Thr Phe Thr Ser Asp Tyr Ser Lys Tyr Leu Asp Glu
1               5                   10                  15

Arg Arg Ala Lys Asp Phe Ile Glu Trp Leu Glu Lys Ala
            20                  25

<210> SEQ ID NO 55
<211> LENGTH: 29
<212> TYPE: PRT
<213> ORGANISM: Artificial Sequence
<220> FEATURE:
<223> OTHER INFORMATION: Synthetic construct

```
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (17)..(17)
<223> OTHER INFORMATION: ([17-carboxy-heptadecanoyl]-isoGlu)
<220> FEATURE:
<221> NAME/KEY: MOD_RES
<222> LOCATION: (29)..(29)
<223> OTHER INFORMATION: NH2

<400> SEQUENCE: 55

His Xaa Gln Gly Thr Phe Thr Ser Asp Tyr Ser Lys Tyr Leu Asp Glu
 1               5                  10                  15

Lys Ala Ala Lys Asp Phe Ile Glu Trp Leu Glu Ser Ala
            20                  25

<210> SEQ ID NO 56
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (17)..(17)
<223> OTHER INFORMATION: ([17-carboxy-heptadecanoyl]-isoGlu-Peg3-Peg3)
<220> FEATURE:
<221> NAME/KEY: MOD_RES
<222> LOCATION: (29)..(29)
<223> OTHER INFORMATION: NH2

<400> SEQUENCE: 56

His Xaa Gln Gly Thr Phe Thr Ser Asp Tyr Ser Lys Tyr Leu Asp Glu
 1               5                  10                  15

Lys Arg Ala Lys Asp Phe Ile Glu Trp Leu Glu Ser Ala
            20                  25

<210> SEQ ID NO 57
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (17)..(17)
<223> OTHER INFORMATION: ([17-carboxy-heptadecanoyl]-isoGlu-Peg3-Peg3)
<220> FEATURE:
<221> NAME/KEY: MOD_RES
<222> LOCATION: (29)..(29)
```

```
<223> OTHER INFORMATION: NH2

<400> SEQUENCE: 57

His Xaa His Gly Thr Phe Thr Ser Asp Tyr Ser Lys Tyr Leu Asp Glu
1               5                   10                  15

Lys Arg Ala Lys Asp Phe Ile Glu Trp Leu Glu Ser Ala
            20                  25

<210> SEQ ID NO 58
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (17)..(17)
<223> OTHER INFORMATION: ([17-carboxy-heptadecanoyl]-isoGlu)
<220> FEATURE:
<221> NAME/KEY: MOD_RES
<222> LOCATION: (29)..(29)
<223> OTHER INFORMATION: NH2

<400> SEQUENCE: 58

His Xaa Gln Gly Thr Phe Thr Ser Asp Tyr Ser Lys Tyr Leu Asp Glu
1               5                   10                  15

Lys Ala Ala Lys Asp Phe Ile Glu Trp Leu Glu Ser Ala
            20                  25

<210> SEQ ID NO 59
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (17)..(17)
<223> OTHER INFORMATION: ([17-carboxy-heptadecanoyl]-isoGlu)
<220> FEATURE:
<221> NAME/KEY: MOD_RES
<222> LOCATION: (29)..(29)
<223> OTHER INFORMATION: NH2

<400> SEQUENCE: 59

His Xaa Gln Gly Thr Phe Thr Ser Asp Tyr Ser Lys Tyr Leu Asp Glu
1               5                   10                  15

Lys Arg Ala Lys Asp Phe Ile Glu Trp Leu Glu Ser Ala
            20                  25

<210> SEQ ID NO 60
<211> LENGTH: 29
<212> TYPE: PRT
<213> ORGANISM: Artificial Sequence
```

```
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (24)..(24)
<223> OTHER INFORMATION: ([17-carboxy-heptadecanoyl]-isoGlu-GSGSGG)
<220> FEATURE:
<221> NAME/KEY: MOD_RES
<222> LOCATION: (29)..(29)
<223> OTHER INFORMATION: NH2

<400> SEQUENCE: 60

His Xaa Gln Gly Thr Phe Thr Ser Asp Tyr Ser Lys Tyr Leu Asp Glu
1               5                   10                  15

Arg Ala Ala Lys Asp Phe Ile Lys Trp Leu Glu Ser Ala
            20                  25

<210> SEQ ID NO 61
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (24)..(24)
<223> OTHER INFORMATION: ([17-carboxy-heptadecanoyl]-isoGlu-GSGSGG)
<220> FEATURE:
<221> NAME/KEY: MOD_RES
<222> LOCATION: (29)..(29)
<223> OTHER INFORMATION: NH2

<400> SEQUENCE: 61

His Xaa Gln Gly Thr Phe Thr Ser Asp Tyr Ser Lys Tyr Leu Asp Glu
1               5                   10                  15

Arg Ala Ala Lys Asp Phe Ile Lys Trp Leu Glu Ser Ala
            20                  25

<210> SEQ ID NO 62
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (24)..(24)
<223> OTHER INFORMATION: ([17-carboxy-heptadecanoyl]-isoGlu-GSGSGG)
<220> FEATURE:
```

<221> NAME/KEY: MOD_RES
<222> LOCATION: (29)..(29)
<223> OTHER INFORMATION: NH2

<400> SEQUENCE: 62

His Xaa Gln Gly Thr Phe Thr Ser Asp Tyr Ser Lys Tyr Leu Asp Glu
1               5                   10                  15

Arg Arg Ala Lys Asp Phe Ile Lys Trp Leu Glu Ser Ala
            20                  25

<210> SEQ ID NO 63
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (28)..(28)
<223> OTHER INFORMATION: ([17-carboxy-heptadecanoyl]-isoGlu-GSGSGG)
<220> FEATURE:
<221> NAME/KEY: MOD_RES
<222> LOCATION: (29)..(29)
<223> OTHER INFORMATION: NH2

<400> SEQUENCE: 63

His Xaa Gln Gly Thr Phe Thr Ser Asp Tyr Ser Lys Tyr Leu Asp Glu
1               5                   10                  15

Arg Ala Ala Lys Asp Phe Ile Glu Trp Leu Glu Lys Ala
            20                  25

<210> SEQ ID NO 64
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Ac4c
<220> FEATURE:
<221> NAME/KEY: MOD_RES
<222> LOCATION: (28)..(28)
<223> OTHER INFORMATION: ([17-carboxy-heptadecanoyl]-isoGlu-GSGSGG)
<220> FEATURE:
<221> NAME/KEY: MOD_RES
<222> LOCATION: (29)..(29)
<223> OTHER INFORMATION: NH2

<400> SEQUENCE: 64

His Xaa Gln Gly Thr Phe Thr Ser Asp Tyr Ser Lys Tyr Leu Asp Glu
1               5                   10                  15

Arg Arg Ala Lys Asp Phe Ile Glu Trp Leu Glu Lys Ala
            20                  25

<210> SEQ ID NO 65
<211> LENGTH: 29

```
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is selected from Aib, Ala, D-Ala, Ser,
      N-Me-Ser, Ac3c, Ac4c or Ac5c
<220> FEATURE:
<221> NAME/KEY: MISC_FEATURE
<222> LOCATION: (3)..(3)
<223> OTHER INFORMATION: Xaa is selected from Gln or His
<220> FEATURE:
<221> NAME/KEY: MISC_FEATURE
<222> LOCATION: (17)..(17)
<223> OTHER INFORMATION: Psi is a residue of Lys, Arg, Orn or Cys in
      which the side chain is conjugated to a substituent having the
      formula -Z2-Z1, wherein Z1 and Z2 are as defined in
      US 2015-0111826

<400> SEQUENCE: 65

His Xaa Xaa Gly Thr Phe Thr Ser Asp Tyr Ser Lys Tyr Leu Asp Ser
1               5                   10                  15
Xaa Ala Ala His Asp Phe Val Glu Trp Leu Leu Ser Ala
            20                  25

<210> SEQ ID NO 66
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (17)..(17)
<223> OTHER INFORMATION: Psi is is a residue of Lys, Arg, Orn or Cys
      in which the side chain is conjugated to a substituent having
      the formula -Z2Z1, wherein Z1 and Z2 are as defined in
      US 2015-0111826

<400> SEQUENCE: 66

His Xaa Gln Gly Thr Phe Thr Ser Asp Tyr Ser Lys Tyr Leu Asp Ser
1               5                   10                  15
Xaa Ala Ala His Asp Phe Val Glu Trp Leu Leu Ser Ala
            20                  25

<210> SEQ ID NO 67
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (17)..(17)
<223> OTHER INFORMATION: ([15-carboxy-pentadecanoyl]-isoGlu)

<400> SEQUENCE: 67

His Xaa Gln Gly Thr Phe Thr Ser Asp Tyr Ser Lys Tyr Leu Asp Ser
1               5                   10                  15
Lys Ala Ala His Asp Phe Val Glu Trp Leu Leu Ser Ala
            20                  25
```

<210> SEQ ID NO 68
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (17)..(17)
<223> OTHER INFORMATION: Psi is a residue of Lys, Arg, Orn or Cys in
      which the side chain is conjugated to a substituent having the
      formula -Z2Z1, wherein Z1 and Z2 are as defined in US 2015-0111826
<220> FEATURE:
<221> NAME/KEY: MOD_RES
<222> LOCATION: (29)..(29)
<223> OTHER INFORMATION: NH2

<400> SEQUENCE: 68

His Xaa Gln Gly Thr Phe Thr Ser Asp Tyr Ser Lys Tyr Leu Asp Ser
1               5                   10                  15
Xaa Ala Ala His Asp Phe Val Glu Trp Leu Leu Ser Ala
            20                  25

<210> SEQ ID NO 69
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MOD_RES
<222> LOCATION: (17)..(17)
<223> OTHER INFORMATION: ([15-carboxy-pentadecanoyl]-isoGlu)
<220> FEATURE:
<221> NAME/KEY: MOD_RES
<222> LOCATION: (29)..(29)
<223> OTHER INFORMATION: NH2

<400> SEQUENCE: 69

His Xaa Gln Gly Thr Phe Thr Ser Asp Tyr Ser Lys Tyr Leu Asp Ser
1               5                   10                  15
Lys Ala Ala His Asp Phe Val Glu Trp Leu Leu Ser Ala
            20                  25

<210> SEQ ID NO 70
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Hydrogen
<220> FEATURE:

```
<221> NAME/KEY: MOD_RES
<222> LOCATION: (2)..(2)
<223> OTHER INFORMATION: 2-methyl
<220> FEATURE:
<221> NAME/KEY: MOD_RES
<222> LOCATION: (20)..(20)
<223> OTHER INFORMATION: [17-Carboxy-heptadecanoyl]-isoGlu-Peg3-Peg3)
<220> FEATURE:
<221> NAME/KEY: MOD_RES
<222> LOCATION: (31)..(31)
<223> OTHER INFORMATION: OH

<400> SEQUENCE: 70

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```

The invention claimed is:

1. A compound having the formula:

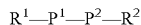

wherein

R$^1$ is H, C$_{1-4}$ alkyl, acetyl, formyl, benzoyl or trifluoroacetyl;

R$^2$ is OH or NH$_2$;

P$^1$ is a peptide having the sequence:

wherein:

X2 is selected from Aib, Ala, D-Ala, Ser, N-Me-Ser, Ac3c, Ac4c and Ac5c; and

X3 is selected from Gln and His;

P$^2$ is absent or is a sequence of 1-20 amino acid units independently selected from the group consisting of Ala, Leu, Ser, Thr, Tyr, Cys, Glu, Lys, Arg, Dbu, Dpr and Orn;

or a pharmaceutically acceptable salt thereof; and

ψ is a residue of Lys, Arg, Orn or Cys in which the side chain is conjugated to a substituent having the formula —Z$^2$—Z$^1$;

—Z$^1$ is a fatty chain having a polar group at one end of the chain and connected via a bond to Z$^2$ at the end of the chain distal from the polar group, and wherein —Z$^1$ is selected from carboxyphenoxynonanoyl, 13-carboxy-tridecanoyl, 15-carboxy-pentadecanoyl and 17-carboxy-heptadecanoyl-; and —Z$^2$— is a spacer selected from:

isoGlu, isoGlu-Peg3-Peg3, isoGlu-Peg4-Peg4, Peg3-Peg3-isoGlu, isoGlu-Gly-Ser-Gly-Ser-Gly-Gly (isoGlu-GSGSGG), and Ala-Ala-Peg3-Peg3 (AA-Peg3-Peg3);

or a pharmaceutically acceptable salt thereof.

2. A compound according to claim 1 wherein P$^1$ has the sequence:

3. A compound according to claim 2 which is:

4. A compound according to claim 1 wherein Z$^1$—Z$^2$ is selected from:
   (i) [17-Carboxy-heptadecanoyl]-isoGlu-Peg3-Peg3;
   (ii) [17-Carboxy-heptadecanoyl]-isoGlu;
   (iii) [13-Carboxy-tridecanoyl]-isoGlu-Peg3-Peg3;
   (iv) [Carboxyphenoxynonanoyl]-isoGlu-Peg3-Peg3;
   (v) [13-Carboxy-tridecanoyl]-isoGlu-Peg4-Peg4;
   (vi) [17-Carboxy-heptadecanoyl]-Peg3-Peg3-isoGlu;
   (vii) [17-Carboxy-heptadecanoyl]-isoGlu-GSGSGG; and
   (viii) [17-Carboxy-heptadecanoyl]-AA-Peg3-Peg3.

5. A compound according to claim 1 wherein P1 has the sequence: H-Aib-QGTFTSDYSKYLDS-K([15-carboxy-pentadecanoyl]-isoGlu)-AAHDFVEWLLSA.

6. A compound according to claim 5 which is: H-H-Aib-QGTFTSDYSKYLDS-K([15-carboxy-pentadecanoyl]-isoGlu)-AAHDFVEWLLSA-NH$_2$.

7. A compound according to claim 1 wherein Z$^2$—Z$^1$ is [17-carboxy-heptadecanoyl]-isoGlu-Peg3-Peg3 or [17-carboxy-heptadecanoyl]-isoGlu-GSGSGG.

8. A composition comprising a compound according to claim 1 in admixture with a carrier.

9. A composition according to claim 8 wherein the composition is a pharmaceutical composition, and the carrier is a pharmaceutically acceptable carrier.

10. A method of preventing weight gain or promoting weight loss in an individual in need thereof, said method comprising administering to the individual a compound of claim 1.

11. A method of lowering circulating LDL levels, and/or increasing HDL/LDL ratio in an individual in need thereof, said method comprising administering to the individual a compound of claim 1.

12. A method of treating a condition caused or characterised by excess body weight, said method comprising administering to the individual a compound of claim 1.

13. A method of preventing or treating obesity, morbid obesity, morbid obesity prior to surgery, obesity linked inflammation, obesity linked gallbladder disease, obesity induced sleep apnea, diabetes, metabolic syndrome, hypertension, atherogenic dyslipidemia, atherosclerosis, arteriosclerosis, coronary heart disease, peripheral artery disease, stroke, or microvascular disease, said method comprising administering to the individual a compound of claim 1.

14. A method of preventing weight gain or promoting weight loss in an individual in need thereof; lowering circulating LDL levels, and/or increasing HDL/LDL ratio in an individual in need thereof; treating a condition caused or characterised by excess body weight; or preventing or treating obesity, morbid obesity, morbid obesity prior to surgery, obesity linked inflammation, obesity linked gallbladder disease, obesity induced sleep apnea, diabetes, metabolic syndrome, hypertension, atherogenic dyslipidemia, atherosclerosis, arteriosclerosis, coronary heart disease, peripheral artery disease, stroke, or microvascular disease, said method comprising administering to the individual a compound of claim 1 as part of a combination therapy together with an agent for treatment of diabetes, obesity, dyslipidemia or hypertension.

15. The method of claim 14, wherein the agent for treatment of diabetes is selected from the group consisting of a biguanide (e.g. metformin), a sulfonylurea, a meglitinide or glinide (e.g. nateglinide), a DPP-IV inhibitor, an SGLT2 inhibitor, a glitazone, a different GLP-1 agonist, an insulin, and an insulin analogue.

16. The method of claim 14, wherein the agent for treatment of obesity is selected from the group consisting of a glucagon-like peptide receptor 1 agonist, a peptide YY receptor agonist or analogue thereof, a cannabinoid receptor 1 antagonist, a lipase inhibitor, a melanocortin receptor 4 agonist, a melanin concentrating hormone receptor 1 antagonist, phentermine, a combination of norepinephrine/dopamine reuptake inhibitor and opioid receptor antagonist (e.g. a combination of phentermine and topiramate), a combination of bupropion and naltrexone, and a serotonergic agent.

17. The method of claim 14, wherein the agent for treatment of hypertension is selected from the group consisting of an angiotensin-converting enzyme inhibitor, an angiotensin II receptor blocker, a diuretic, a beta-blocker, and a calcium channel blocker.

18. The method of claim 14, wherein the agent for treatment of dyslipidemia is selected from the group consisting of a statin, a fibrate, a niacin, and a cholesterol absorption inhibitor.

19. A therapeutic kit comprising a compound according to claim 1 optionally in admixture with a carrier.

20. A method of producing a compound according to claim 1, the method comprising expressing a precursor peptide sequence from a nucleic acid construct that encodes the precursor peptide, recovering the expression product, and modifying the precursor peptide to yield a compound according to claim 1.

21. A method according to claim 20 comprising modifying the precursor peptide to introduce the substituent at residue $\psi$.

* * * * *